(12) United States Patent
Wang et al.

(10) Patent No.: US 8,901,159 B2
(45) Date of Patent: Dec. 2, 2014

(54) INHIBITION OF INFLAMMATION BY SIMULTANEOUS BLOCKADE OF MULTIPLE PROSTANOID RECEPTORS

(75) Inventors: Jenny W. Wang, Irvine, CA (US); David F. Woodward, Lake Forest, CA (US); Ming Ni, Laguna Niguel, CA (US); Jose L. Martos, Basildon Essex (GB); William R. Carling, Bishop's Stortford (GB)

(73) Assignee: Allergan, Inc., Irvine, CA (US)

( * ) Notice: Subject to any disclaimer, the term of this patent is extended or adjusted under 35 U.S.C. 154(b) by 208 days.

(21) Appl. No.: 13/171,020

(22) Filed: Jun. 28, 2011

(65) Prior Publication Data
US 2012/0077857 A1 Mar. 29, 2012

Related U.S. Application Data

(60) Provisional application No. 61/360,738, filed on Jul. 1, 2010, provisional application No. 61/410,153, filed on Nov. 4, 2010.

(51) Int. Cl.
*A61K 31/42* (2006.01)
*A61K 31/422* (2006.01)

(52) U.S. Cl.
CPC .................. *A61K 31/422* (2013.01)
USPC ........................................... 514/374

(58) Field of Classification Search
CPC ................................... A61K 31/422
USPC ........................................... 514/374
See application file for complete search history.

(56) References Cited

U.S. PATENT DOCUMENTS

| | | | | |
|---|---|---|---|---|
| 5,605,917 | A * | 2/1997 | Ogletree | 514/365 |
| 7,045,634 | B2 * | 5/2006 | Krauss et al. | 548/236 |
| 7,217,725 | B2 * | 5/2007 | Krauss et al. | 514/374 |
| 2004/0162333 | A1 | 8/2004 | Mezaache | |
| 2005/0054699 | A1 | 3/2005 | Krauss | |
| 2005/0065200 | A1 | 3/2005 | Woodward | |
| 2006/0106078 | A1 | 5/2006 | Krauss | |

FOREIGN PATENT DOCUMENTS

WO 2005-079793 9/2005

OTHER PUBLICATIONS

Misra et al. "Intertphenylene 7—oxabicyclo(2,2,1)hepatane oxazoles—Highly potent selective and long acting thromboxane A2 receptor antagonists," J. Med. Chem. 1993, vol. 36, pp. 1401-1407.*
A. Mocali et al, 2004, Increased Plasma Levels of Soluble CD40, Together With the Decrease of TGFB1, as Possible Differential Markers of Alzheimer Disease, Experimental Gerontology, 39, 1555-1561.

Alma Zernecke et al, 2006, Deficiency in CCR5 but not CCR1 Protects Against Neointima Formation in Atherosclerosis-Prone Mice: Involvement of IL-10, Blood, 106, 4240-4243.
Andor Pivarcsi et al, 2005, Chemokine Networks in Atopic Dermatitis: Traffic Signals of Disease, Current Allergy and Asthma Reports, 5, 284-290.
Ann Cornish et al, 2009, G-CSF and GM-CSF as Therapeutic Targets in Rheumatoid Arthritis, Nat Rev Rheumatol, 5, 554-559.
C. Y. Ho et al, 2003, Suppressive effect of combination treatment of leflunomide and methotrexate on chemokine expression in patients with rheumatoid arthritis, Clin Exp Immunol, 133, 132-138.
Christian A. Gleissner et al, 2008, Platelet Chemokines in Vascular Disease, ATVB in Focus Chemokines in Atherosclerosis, Thrombosis, and Vascular Biology, 28, 1920-1927.
E.W. St. Clair et al, 2004, Genetic Polymorphisms in Tumor Necrosis Factor (TNF)-a and TNF-B in a Population-Based Study of Systemic Lupus Erythematosus: Associations and Interaction with the Interleukin-1a-889 C/T Polymorphism, Human Immunology, 65, 622-631.
Gilles Garcia et al, 2005, New Chemokine Targets for Asthma Therapy, Current Allergy and Asthma Reports, 5, 155-160.
Gisela Orozco et al, 2010, Association of CD40 With Rheumatoid Arthritis Confirmed in a Large UK Case-Control Study, Ann Theum Dis, 69, 813-816.
H. Schmilovitz-Weiss et al, 2004, Lamivudine Treatment for Acute Severe Hepatitis B: A Pilot Study, Liver International, 24, 547-551.

(Continued)

*Primary Examiner* — Shengjun Wang
(74) *Attorney, Agent, or Firm* — Mark D. Kafka

(57) ABSTRACT

The present invention provides a method for treating inflammation in a patient in need thereof comprising administering to said patient an effective amount of a compound according to formula

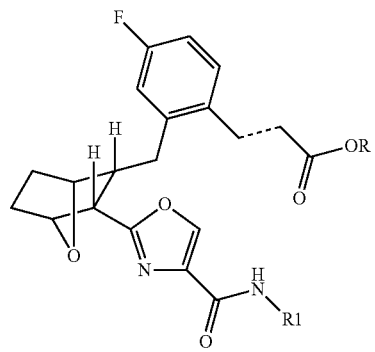

wherein R is H or lower alkyl, R1 is hydrocarbyl or substituted hydrocarbyl and the broken line represents a saturated or unsaturated bond, i.e a double bond. Preferably, R1 is an alkyl. More preferably, R1 is a n-alkyl or a cycloalkyl-n-alkyl, e.g. a cyclohexyl-n-alkyl, e.g. n-octyl, n-nonyl or cyclohexyl-n-butyl radical and prodrugs, isomers and pharmaceutically acceptable salts thereof.

18 Claims, 15 Drawing Sheets

(56) References Cited

OTHER PUBLICATIONS

H.E. Barksby et al, May 18, 2007, The Expanding Family of Interleukin-1 Cytokines and Their Role in Destructive Inflammatory Disorders, Clinical and Experimental Immunology, 149, 217-225.

Jo Eyles et al, 2006, Granulocyte Colony-Stimulating Factor and Neutrophils-Forgotten Mediators of Inflammatory Disease, Nature Clinical Practice Rheumatology, 2 (9), 500-510.

Kazuhiro Komura et al, 2007, Increased Serum Soluble CD40 Levels in Patients with Systemic Sclerosis, Journal of Rheumatology, 34 (2), 353-358.

Kiyoshi Matsui et al, 2003, Pathophysiological Roles for IL-18 in Inflammatory Arthritis, Expert Opin. Ther. Targets, 7(6), 701-724.

M.L. Castellani et al, 2007, Anti-Chemokine Therapy for Inflammatory Diseases, International Journal of Immunopathology and Pharmacology, vol. 20, No. 3, 447-453.

Michael Van Der Linden et al, 2009, Association of a Single-Nucleotide Polymorphism in CD40 With the Rate of joint Destruction in Rheumatoid Arthritis, Arthritis & Rheumatism, 60 (8), 2242-2247.

Muhammad Rizvi et al, 2008, CD40-CD40 Ligand Interactions in Oxidative Stress, Inflammation and Vascular Disease, Trends in Molecular Medicine, 14 (12), 530-538.

P. Conti et al, 2001, MCP-1 and RANTES Are Mediators of Acute and Chronic Inflammation, Allergy and Asthma Proc, 22, 133-137.

R.F. Schwabe et al, 1999, Soluble CD40 in the Serum of Healthy Donors, Patients With Chronic Renal Failure, Haemodialysis and Chronic Ambulatory Peritoneal Dialysis (CAPD) Patients, Clin Exp Immunol, 117, 153-158.

Sheng-Ming Dai et al, 2007, Cellular Targets of Interleukin-18 in Rheumatoid Arthritis, Ann Rheum Dis, 66, 1411-1418.

Takuji Iwamoto et al, 2008, Molecular aspects of rheumatoid arthritis: chemokines in the joints of patients, The FEBS Journal, 275, 4448-4455.

Xu-Feng Qi et al, 2009, The adenylyl cyclase-cAMP system suppresses TARC/CCL17 and MDC/CCL22 production through p38 MAPK and NF-KB in HaCaT keratinocytes, Molecular Immunology, 46, 1925-1934.

Patent Cooperation Treaty, Notification of Transmittal of the International Search Report and the Written Opinion of the International Searching Authority, or the Declaration, Form PCT/ISA/220, Int. App. No. PCT/US2011/042851, Jan. 23, 2012.

* cited by examiner

Figure 14

Anti-inflammation Summary

| Group (n) Animal ID | EAU inducer | | EAU treatment | | | End point day | Results | | | | | |
|---|---|---|---|---|---|---|---|---|---|---|---|---|
| | | | compound | | systemic | | Clinic (Score) | | AQ.H protein (mg/mL) | | AQ.H Cells (cells/mL) | |
| | day | inducer | tested article | adm. day | Dose (ip) | | Mean ±SD | p | Mean ±SD | p | Mean ±SD | p |
| 1 (n=8) 1284-1291 | 0 | M18 | vehicle | 4 to 13 | 1ml/kg | 14 | 2.19 ±0.54 | - | 12.29 ±5.29 | - | 52916.67 ±29555.74 | - |
| 2 (n=8) 1292-1299 | 0 | M18 | Example 1 | 4 to 13 | 30mg/kg | 14 | 1.25 ±0.77 | 0.000 | 3.63 ±1.01 | 0.006 | 18333.33 ±18073.92 | 0.039 |
| 3 (n=8) 1300-1307 | 0 | M18 | Example 8 | 4 to 13 | 30mg/kg | 14 | 1.47 ±0.99 | 0.018 | 10.68 ±4.61 | 0.506 | 45833.33 ±31371.43 | 0.696 |
| 4 (n=8) 1308-1315 | 0 | M18 | SC-51322 | 4 to 13 | 10mg/kg | 14 | 2.00 ±0.77 | 0.681 | 6.21 ±3.61 | 0.046 | 35416.67 ±26618.45 | 0.307 |
| 5 (n=8) 1316-1323 | 0 | M18 | Example 8 + SC-51322 | 4 to 13 | 1ml/kg | 14 | 0.89 ±0.96 | 0.000 | 4.55 ±6.84 | 0.078 | 22800 ±24078.21 | 0.068 |

M18: M18 peptide of S-Ag      Structure: DTNLASSTIIKEGIDKTV

Figure 15

Angiostatic Efficacy – Prostaglandin Receptor Antagonists on Rat Laser CNV

INHIBITION OF INFLAMMATION BY SIMULTANEOUS BLOCKADE OF MULTIPLE PROSTANOID RECEPTORS

CROSS REFERENCE TO RELATED APPLICATIONS

This application claims the benefit of U.S. Provisional Patent Application Ser. Nos. 61/360,738 filed on Jul. 1, 2010 and U.S. Provisional Patent Application Ser. Nos. 61/410,153 filed on Nov. 4, 2010 both of which are hereby incorporated by reference in its entirety.

BACKGROUND OF THE INVENTION

1. Field of the Invention

The present invention relates to compounds that show an anti-inflammatory action and are useful as pharmaceuticals 2. Summary of the Related Art At present, the majority of medicines widely used as anti-inflammatory agents are non-steroid anti-inflammatory drugs (NSAIDs) that have, as the mechanism of action, an inhibitory action on cyclooxygenases (COXs) that is involved in the biosynthesis of prostanoids. However, since prostanoid synthesis activity is present in various tissues in the living body and governs the homeostasis thereof, various side effects are induced when NSAID is administered. For example, PGE2 demonstrates the action of maintaining blood flow in the stomach and kidneys, whereas administration of NSAIDs makes it difficult to maintain local blood flow, thereby causing gastric or renal disorders.

Under such circumstances, the presence of a COX isozyme has been confirmed. In order to distinguish it from the previously identified COX, the conventional type has been named COX-1, while the more recently discovered isozyme has been named COX-2. In addition, this COX-2 has been shown to be induced during inflammation and hardly be expressed under normal circumstances. It has also been shown that conventional NSAID are able to non-specifically inhibit both COX-1 and COX-2 enzymes. Therefore, a compound having COX-2 inhibitory action would be useful as an anti-inflammatory agent.

There are currently several compounds that are known to preferentially inhibit COX-2 whilst having significantly less COX-1 inhibitory activity. However, the actions of these compounds are not satisfactory and since some of them do not have an adequate water solubility or oral absorption, there remains a need for a drug that demonstrates more effective COX-2 inhibitory action.

Vioxx or 4-[4-(methylsulfonyl)phenyl]-3-phenyl-2(5H)-furanone (rofecoxib) belongs to the group of NSAIDs known as COX-2 selective inhibitors or coxibs (CycloOXygenase-2 InhiBitors). Being COX-2 selective means that these drugs act preferentially on one form of the cyclooxygenase (COX) enzyme, namely the COX-2, whereas earlier NSAIDs inhibited both COX-1 and COX-2 with little if any selectivity. This specificity allows rofecoxib and other COX-2 inhibitors to reduce inflammation and pain while minimizing undesired gastrointestinal adverse effects, e.g. peptic ulcers are common with non-selective NSAIDs such as aspirin, naproxen, and ibuprofen.

Moreover it has been shown that there is an increased risk of cardiovascular events associated with the use of rofecoxib, valdecoxib and parecoxib and these compounds were withdrawn from the market.

Nevertheless, nonsteroidal anti-inflammatory drugs (NSAIDs) have been successfully administered to treat pain and inflammation for many years. The analgesic, antipyretic and anti-inflammatory properties of aspirin and other NSAIDs were explained by the inhibition of prostanoid synthesis by suppressing cyclooxygenase (COX) activity. This finding not only explains the mechanism of action of NSAIDs, but also reveals a useful pharmacological tool for evaluating the physiological role of prostanoids by COX inhibition. NSAIDS are the most frequently used drugs worldwide, based on the fact that they are administered to treat large numbers of patients for many systemic pathological conditions, including chronic polyarthritis, psoriatic arthritis, ankylosing spondylitis, osteoarthritis, gout, inflammatory soft tissue rheumatism, lower back pain, post-operative and post-traumatic inflammation, thrombophlebitis, vasculitis, and certainly rheumatoid arthritis Dermatologic conditions including erythema nodosum, nodular acne, prurigo nodularis, palmoplantar pustulosis, and psoriasis that could lead to psoriatic arthritis, have also been treated by NSAIDs. However, as noted above, long-term use of NSAIDs is associated with gastrointestinal (GI) erosion and renal failure.

Prostanoids (PGs) are widely distributed throughout the gastrointestinal tract. Inhibition of PG synthesis is the principal underlying mechanism for GI mucosal erosion. Endogenous prostaglandin $E_2$ ($PGE_2$), derived from both COX-1 and COX-2, has been shown to be involved in mucosal defense by decreasing gastric acid secretion, which is mediated by prostaglandin E2 receptor (EP) type 3 ($EP_3$) in rats. $PGE_2$ has a dual action on gastric acid secretion in rats, with the inhibitory effect mediated by $EP_3$ receptors and the stimulatory effect through $EP_4$ receptors. In mice, $EP_3$ but not $EP_1$ receptors are essential for acid-induced duodenal $HCO_3^-$ secretion and mucosal integrity. Endogenous $PGI_2$, also has a protective role in gastric mucosal integrity in mice. Unlike in rodents, $EP_1$ receptors are not found in any type of cells in the human gastric mucosa.

In the kidney, prostanoids uphold the balance between vasodilatation and vasoconstriction. They also regulate renin secretion, tubular transport processes, and cell fate. $PGI_2$ signaling is essential for maintenance of renal homeostasis and renal function, which is supported by the fact that COX-2 and PGI synthase (PGIS) knockout mouse models display significant disturbances in the kidney. The preferential association between COX-2 and PGIS in $PGI_2$ biosynthesis was evidenced by the fact that the renal phenotype of PGIS knockout mice closely resembles the one shown in COX-2 knockout animals, while no major abnormalities in COX-1 knockout mice were apparent. The same association is also presented in humans. On the other hand, $PGE_2$ regulates renal hemodynamics and salt and water excretion via prostanoid receptors $EP_{1-4}$, where $EP_1$ and $EP_3$ act as constrictors, and $EP_2$ and $EP_4$ as dilators. The bidirectional capacity of $PGE_2$ to modulate vascular tone and epithelial transport allows $PGE_2$ to serve as a buffer to prevent physiological disturbances. Therefore, both $PGE_2$ and $PGI_2$ are crucial prostanoids in regulating normal kidney function. Their inhibition by NSAIDs results in sodium retention and hypertension, which could cause acute renal failure.

Cyclooxygenases (COXs), COX-1 and COX-2, also known as prostanoid H synthases (PGH synthase), are the key enzymes in the synthesis of prostanoids from arachidonic acid released from membrane phospholipids. The major difference between these two enzymes remains that COX-1 is constitutively expressed as a "housekeeping enzyme" involved in physiological functions in many cells, whereas COX-2 is usually expressed inducibly and transiently. Because of the expression patterns of the two isoforms of COX, it was assumed that COX-1-derived prostanoids were involved in regulating physiological functions, whereas COX-2-derived prostanoids played a major role in inflammation or tissue damage. According to this hypothesis, the pharmacological effects of NSAIDs depend on the inhibition of COX-2, whereas the toxic organ-specific effects in GI tissue and kidney are linked to the inhibition of COX-1. Therefore, as noted above, COX-2 selective inhibitors (COXIBs) were developed as anti-inflammatory agents to minimize the side effects associated with NSAIDs. However, in reality, COX-2 also plays a physiological role in certain tissues and organs, and COX-1 may be involved in inflammatory reactions. "Constitutive" expression has also been observed for both isoforms of COX in the kidney, spinal cord, and brain.

While there is no obvious advantage of COXIBs over non-selective NSAIDS in terms of renal toxicity, significantly fewer GI complications have been reported in patients treated with COXIBs. However, selective inhibition of COX-2 causes an imbalance between COX-2 derived $PGI_2$ and COX-1 derived $TXA_2$, which results in serious cardiovascular risk. $TXA_2$ is a major prostanoid released from activated platelets by COX-1 to stimulate platelet aggregation and vasoconstriction. To counter the biological effects of $TXA_2$, $PGI_2$, a dominant product of COX-2 under physiological conditions in vascular endothelial cells, acts as a protective constraint on thrombogenesis, hypertension, and atherogenesis. The imbalance in favor of $TXA_2$ resulting from the clinical use of COXIBs disrupts vascular homeostasis and, thus increases vulnerability to thrombosis, atherosclerosis, and hypertension; particularly in patients genetically susceptible to cardiovascular disease. The withdrawal of the selective COX-2 inhibitors rofecoxib and valdecoxib have emphasized the cardioprotective role of prostacyclin.

Although clearly demonstrated by the long and wide use of the NSAIDs/COXIBs that prostanoids are critical inflammatory mediators, each prostanoid, $PGD_2$, $PGF_{2\alpha}$, $PGI_2$, $TXA_2$, and particularly $PGE_2$, might sometimes be anti-inflammatory. Most importantly, the cardiovascular, renal, and gastrointestinal toxicities associated with the NSAIDs/COXIBs must be addressed. It seems like that $EP_3$ receptors should be spared from blockade because of their roles in GI protection, and IP receptors should be preserved because of their importance in cardiovascular and renal homeostasis, while it might be necessary to block TP receptors because of their cardiovascular liability in clinical use of COXIBs.

Prostamide antagonist are known from published U.S. Patent Application Nos. 2008/0696240, 2005/0054699 and 2006/0106078. PGD2 antagonists are known from published US Patent Application No. 2004/0162333.

An object of the present invention is to provide compounds that have FP, DP, EP1, EP4 and TP inhibitory activity, but lack EP2, EP3 and IP activity and are useful as pharmaceuticals.

SUMMARY OF THE INVENTION

The present invention provides a method for treating inflammation in a patient in need thereof comprising administering to said patient an effective amount of a compound according to formula I

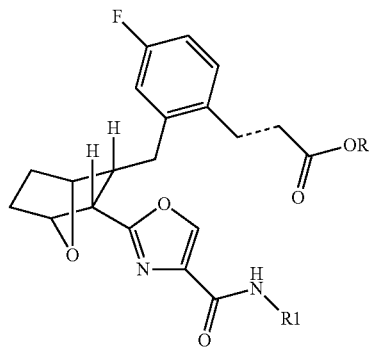

wherein R is H or lower alkyl, R1 is hydrocarbyl or substituted hydrocarbyl and the broken line represents a saturated or unsaturated bond, i.e a double bond. Preferably R1 is an alkyl. More preferably R1 is a n-alkyl or a cycloalkyl-n-alkyl, e.g. a cyclohexyl-n-alkyl, e.g. n-octyl, n-nonyl or cyclohexyl-n-butyl radical.

The inventors of the present application have found that compounds represented by the general formula (1) and prodrugs, isomers, pharmaceutically acceptable salts thereof, i.e. acid and basic salts thereof, have anti-inflammatory action and/are effective in reducing the secretion of certain inflammatory cytokines and/or chemokines, making them useful as pharmaceuticals. It has been shown that simultaneous blockade of multiple potentially pro-inflammatory prostanoid receptors by the compounds of this invention is either superior or at least as good as rofecoxib (a COXIB) and diclofenac (a NSAID) in inhibiting the release of multiple pro-inflammatory cytokines and chemokines The compound of general Formula 1 blocks the following receptors: DP1, EP1, EP4, FP and TP; and produces weak blockade of DP2.

The present invention provides a pharmaceutical composition comprising the compound of formula I and a pharmaceutically-acceptable carrier, in a solid or liquid dosage form, such as tablets, capsules, powders, granules, suppositories, solution, suspension or emulsion.

Said pharmaceutical composition of the present invention may further comprise one or more excipients, disintegrators, lubricants, binders, preservatives, stabilizers and/or osmotic pressure regulating agents.

In addition the present invention provides a pharmaceutical product comprising the above composition wherein said product is packaged and labeled for the treatment of a disease or condition selected from the group consisting of inflammatory diseases and autoimmune diseases, including systemic inflammatory conditions: inflammatory soft tissue rheumatism, psoriatic arthritis and rheumatoid arthritis, chronic polyarthritis, ankylosing spondylitis, gout, thrombophlebitis, vasculitis, renal fibrosis and chronic renal failure, chronic liver diseases, pleurisy, colitis, endometriosis diseases, parasitic diseases, and cancer; cardiovascular related diseases, such as deep vein thrombosis, atherosclerosis, pulmonary fibrosis, hypertension, and hypertriglyceridemia, type 2 diabetes obesity, and atherothrombosis; inflammatory ocular diseases, such as uveitis and age-related macular degeneration; dermatologic conditions, such as atopic dermatitis, polymyositis and dermatomyositis, erythema nodosum, nodular acne, prurigo nodularis, palmoplantar pustulosis, and psoriasis; allergy and asthma, including allergic lung inflammation, lung leukocyte infiltration, bronchial hyper-responsiveness, and allergic rhinitis; bone and cartilage destruction, such as osteoporosis and osteoarthritis; CNS disorders, such as brain inflammation, multiple sclerosis, Alzheimer's disease; and post-operative and post-traumatic inflammation. These exemplified diseases result from the stimulation of the production of proinflammatory cytokines/chemokines, collagenases, metalloproteinases, and other inflammatory mediators; inhibition of plasminogen fibrinolysis and excessive fibrin accumulation; activation of endothelial cells and neutrophils; promotion of T- and B-cell growth; stimulation of bone resorption, as well as angiogenesis in inflamed and cancerous tissues.

Finally, the present invention provides certain novel compounds, which are (E)-3-(2R-{3R-[4-(4-Alkylcarbamoyl)-oxazol-2-yl]-7-oxa-bicyclo[2.2.1]hept-2-ylmethyl}-4-fluoro-phenyl)-acrylic acids and lower alkyl esters thereof. In the above formula, the novel compounds are represented by those compounds wherein the alpha chain comprises a double bond.

Some of embodiments of the invention include but are not limited to:

What is claimed is:

1. A method for treating inflammation in a patient in need thereof comprising administering to said patient an effective amount of a compound according to formula

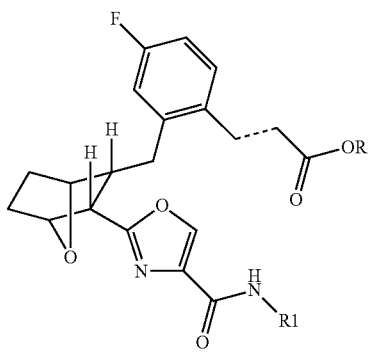

wherein R is H or lower alkyl, R1 is hydrocarbyl or substituted hydrocarbyl and the broken line represents a saturated or unsaturated bond, a double bond, a wherein the formula includes prodrugs, isomers and pharmaceutically acceptable salts thereof.

2. The method of paragraph 1 wherein said compound is

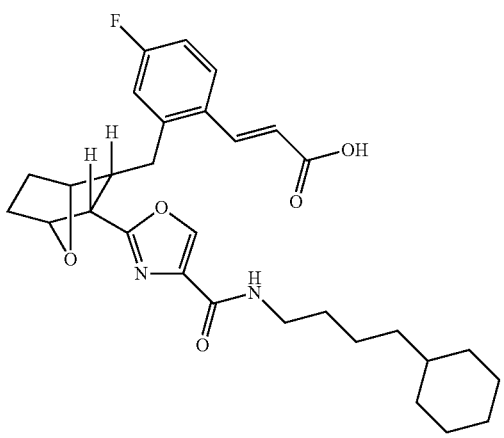 [SMILES: O=C(O)/C=C/c1ccc(F)cc1CC1C2CCC(O2)C1c1nc(C(=O)NCCCCC2CCCCC2)co1]

3. The method of paragraph 2 wherein said method comprises decreasing the secretion of ENA-78 in a patient.

4. The method of paragraph 2 wherein said method comprises decreasing the secretion of IL-8 in a patient.

5. The method of paragraph 2 wherein said method comprises decreasing the secretion of MCP-1 in a patient.

6. The method of paragraph 2 wherein said method comprises decreasing the secretion of PAI-1 in a patient.

7. The method of paragraph 2 wherein said method comprises decreasing the secretion of CD-40 in a patient.

8. The method of paragraph 2 wherein said method comprises decreasing the secretion of G-C—SF in a patient.

9. The method of paragraph 2 wherein said method comprises decreasing the secretion of GM-CSF in a patient.

10. The method of paragraph 2 wherein said method comprises decreasing the secretion of IL-1α in a patient.

11. The method of paragraph 2 wherein said method comprises decreasing the secretion of IL-18 in a patient.

12. The method of paragraph 2 wherein said method comprises decreasing the secretion of MDC in a patient.

13. The method of paragraph 2 wherein said method comprises decreasing the secretion of RANTES in a patient.

14. The method of paragraph 2 wherein said compound is at least as effective as COXIBs and NSAIDs in treating inflammation in a patient in need of such treatment, without causing cardiovascular, renal and/or gastro-intestinal side effects.

15. A method for decreasing the secretion of the cytokine selected from the group consisting of ENA-78, IL-8, MCP-1, PAI-1, TNFα, CD-40, G-CSF, GM-CSF, IL-1α, IL-18, MDC and RANTES in a patient in need thereof comprising administering to a patient an effective amount of a compound according to formula I:

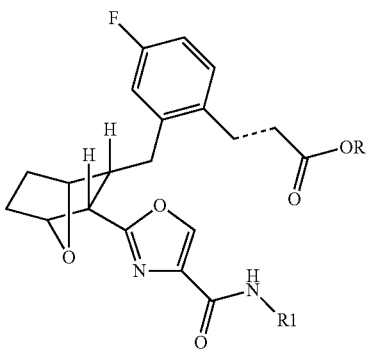

wherein R is H or lower alkyl, R1 is hydrocarbyl or substituted hydrocarbyl and the broken line represents a saturated or unsaturated bond, such as a double bond.

16. The method of paragraph 15 wherein said compound is:

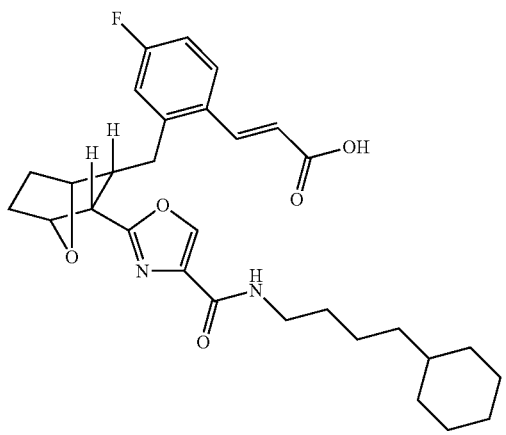 [SMILES: O=C(O)/C=C/c1ccc(F)cc1CC1C2CCC(O2)C1c1nc(C(=O)NCCCCC2CCCCC2)co1]

17. A method according to paragraph 15 wherein said cytokine is ENA-78 and said compound is administered for treating rheumatoid arthritis.

18. A method according to paragraph 15 wherein said cytokine is IL-8 and said compound is administered for treating rheumatoid arthritis.

19. A method according to paragraph 15 wherein said cytokine is MCP-1 and said compound is administered for treating inflammatory diseases characterized by monocytic infiltration, wherein such diseases are selected from the group consisting of RA rheumatoid arthrutus, psoriasis, and atherosclerosis; atopic dermatitis, renal disease; pleurisy; allergy and asthma; colitis; endometriosis; polymyositis and dermatomyositis; uveitis; restenosis; brain inflammation and obesity; diabetes and diabetes-induced atherosclerosis and MCP-1/CCR2-mediated multiple inflammatory diseases.

20. A method according to paragraph 15 wherein said cytokine is CD-40 and said compound is administered for treating rheumatoid arthritis, inflammation, thrombosis and atherosclerosis, chronic renal failure, chronic liver diseases, Alzheimer's disease and systemic sclerosis.

21. A method according to paragraph 15 wherein said cytokine is G-CSF and said compound is administered for treating rheumatoid arthritis, including collagen-induced arthritis and inflammation.

22. A method according to paragraph 15 wherein said cytokine is GM-CGF and said compound is administered for treating rheumatoid arthritis.

23. A method according to paragraph 15 wherein said cytokine is IL-1α and said compound is administered for treating rheumatoid arthritis.

24. A method according to paragraph 15 wherein said cytokine is IL-18 and said compound is administered for treating rheumatoid arthritis, inflammation and bone and cartilage destruction.

25. A method according to paragraph 15 wherein said cytokine is MDC and said compound is administered for treating rheumatoid arthritis, inflammation, thrombosis and atherosclerosis, chronic renal failure, chronic liver diseases, Alzheimer's disease and systemic sclerosis.

26. A method according to paragraph 15 wherein said cytokine is RANTES and said compound is administered for treating rheumatoid arthritis, inflammation, thrombosis and atherosclerosis, asthma, including allergic lung inflammation, lung leukocyte infiltration, bronchial hyper-responsiveness, and the recruitment of eosinophils in the pathogenesis of asthma, and allergic rhinitis, multiple sclerosis, CNS disorders, parasitic disease, cancer, autoimmune and heart diseases.

27. A method according to paragraph 15 wherein said cytokine is PAI-1 and said compound is administered for treating diseases relating to the inhibition of plasminogen fibrinolysis, excessive fibrin accumulation, and the sequential luminal obstruction, thrombus formation, atherosclerotic lesions, vascular inflammation, and pathological evolution of atherosclerotic plaques, deep vein thrombosis, atherosclerosis, renal and pulmonary fibrosis, and cancer; as well as metabolic syndrome with a combination of obesity, insulin resistance, hypertension, hypertriglyceridemia, renal and cardiovascular disease.

28. A method according to paragraph 15 wherein said cytokine is TNFα and said compound is administered for treating diseases resulting from the stimulation of the production of proinflammatory cytokines/chemokines, collagenases, metalloproteinases, and other inflammatory mediators; activation of endothelial cells and neutrophils; promotion T- and B-cell growth, as well as stimulation of bone resorption, the production of local and systemic proinflammatory cytokines/chemokines and serum MMP-3, nitric oxide synthase activity, VEGF release, and angiogenesis in inflamed joints.

29. A method of treating inflammatory diseases and autoimmune diseases, including systemic inflammatory conditions selected from the group consisting of inflammatory soft tissue rheumatism, psoriatic arthritis and rheumatoid arthritis, chronic polyarthritis, ankylosing spondylitis, gout, thrombophlebitis, vasculitis, renal fibrosis and chronic renal failure, chronic liver diseases, pleurisy, colitis, endometriosis diseases, parasitic diseases, and cancer; cardiovascular related diseases, such as deep vein thrombosis, atherosclerosis, pulmonary fibrosis, hypertension, and hypertriglyceridemia, type 2 diabetes obesity, and atherothrombosis; inflammatory ocular diseases, such as uveitis and age-related macular degeneration; dermatologic conditions, such as atopic dermatitis, polymyositis and dermatomyositis, erythema nodosum, nodular acne, prurigo nodularis, palmoplantar pustulosis, and psoriasis; allergy and asthma, including allergic lung inflammation, lung leukocyte infiltration, bronchial hyper-responsiveness, and allergic rhinitis; bone and cartilage destruction, such as osteoporosis and osteoarthritis; CNS disorders, such as brain inflammation, multiple sclerosis, Alzheimer's disease; and post-operative and post-traumatic inflammation.

30. The method of paragraph 29 wherein said compound is

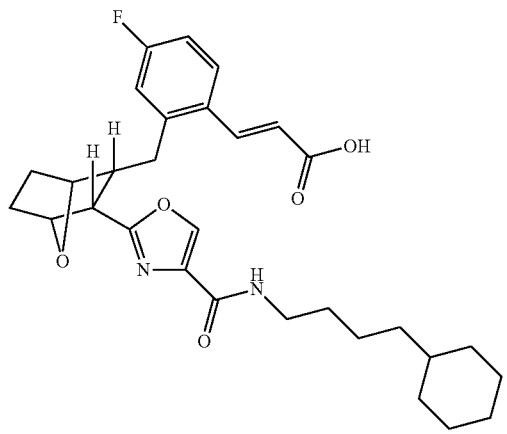 [SMILES: O=C(O)/C=C/c1ccc(F)cc1CC1C2CCC(O2)C1c1nc(C(=O)NCCCCC2CCCCC2)co1]

31. A compound according to formula

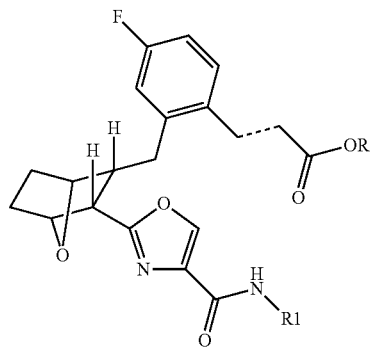

wherein R is H or lower alkyl, R1 is hydrocarbyl or substituted hydrocarbyl and the broken line represents a saturated or an unsaturated bond, a double bond, and the compound includes prodrugs, isomers and pharmaceutically acceptable salts thereof.

BRIEF DESCRIPTION OF THE DRAWINGS

FIG. 14 is a summary of the results obtained in a comparison of a representative compound of the compounds of the present invention and various other PG antagonists in an in-vivo model of inflammation; and, FIG. 15 is a summary of the results obtained in a comparison of a representative compound of the compounds of the present invention and various other PG antagonists in an in vivo model of neovascularization.

DETAILED DESCRIPTION OF THE INVENTION

Figure 1:
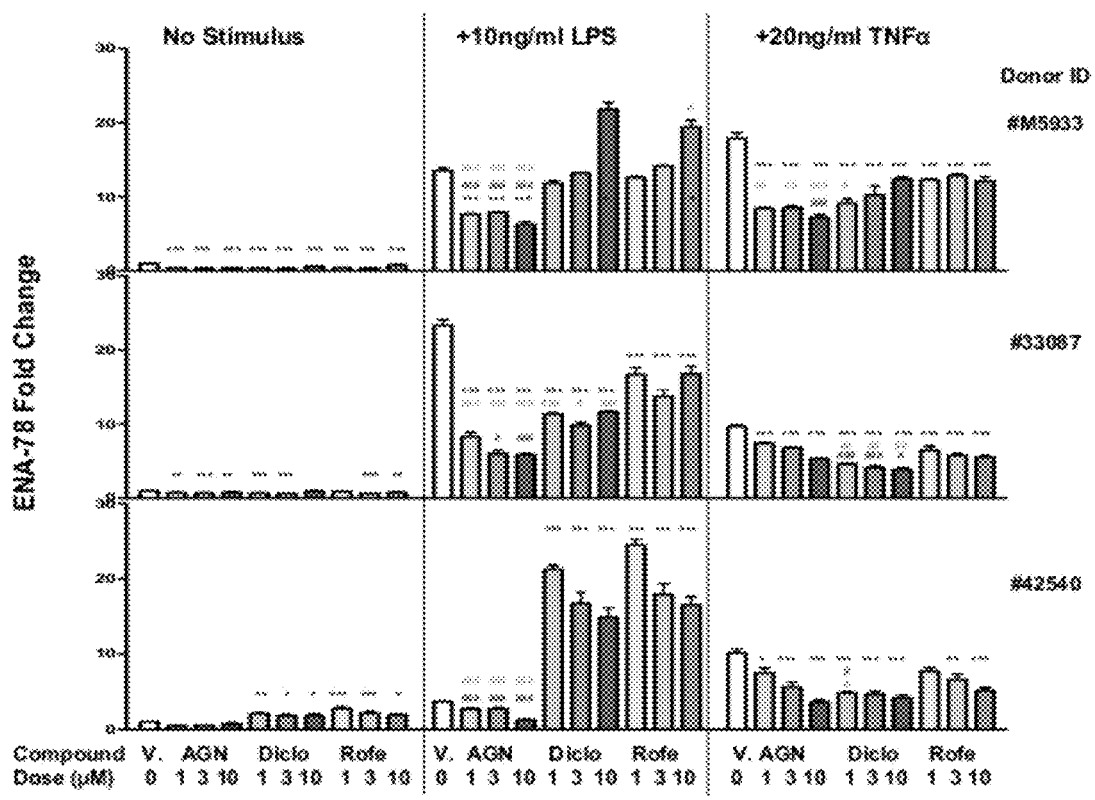
FIG. 1 shows a comparison of a representative compound of this invention, i.e. the compound of Example 1, with diclofenac and rofecoxib in modulating the secretion of ENA-78 from human macrophages stimulated by LPS and TNFα (n=three donors, normalized by cell viability)
Figure 2:
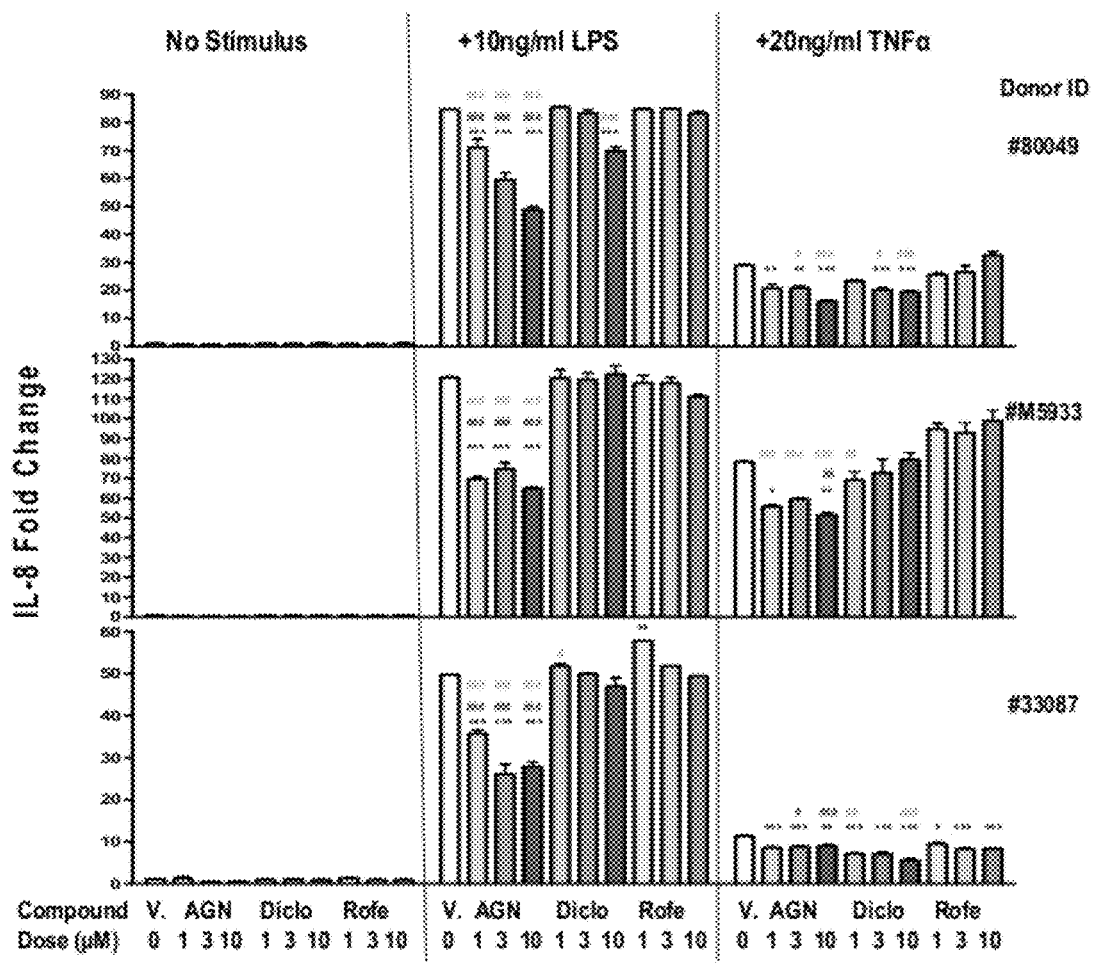
FIG. 2 shows a comparison of this representative compound of this invention with diclofenac and rofecoxib in modulating the secretion of IL-8 from human macrophages stimulated by LPS and TNFα (n=three donors, normalized by cell viability)
Figure 3:
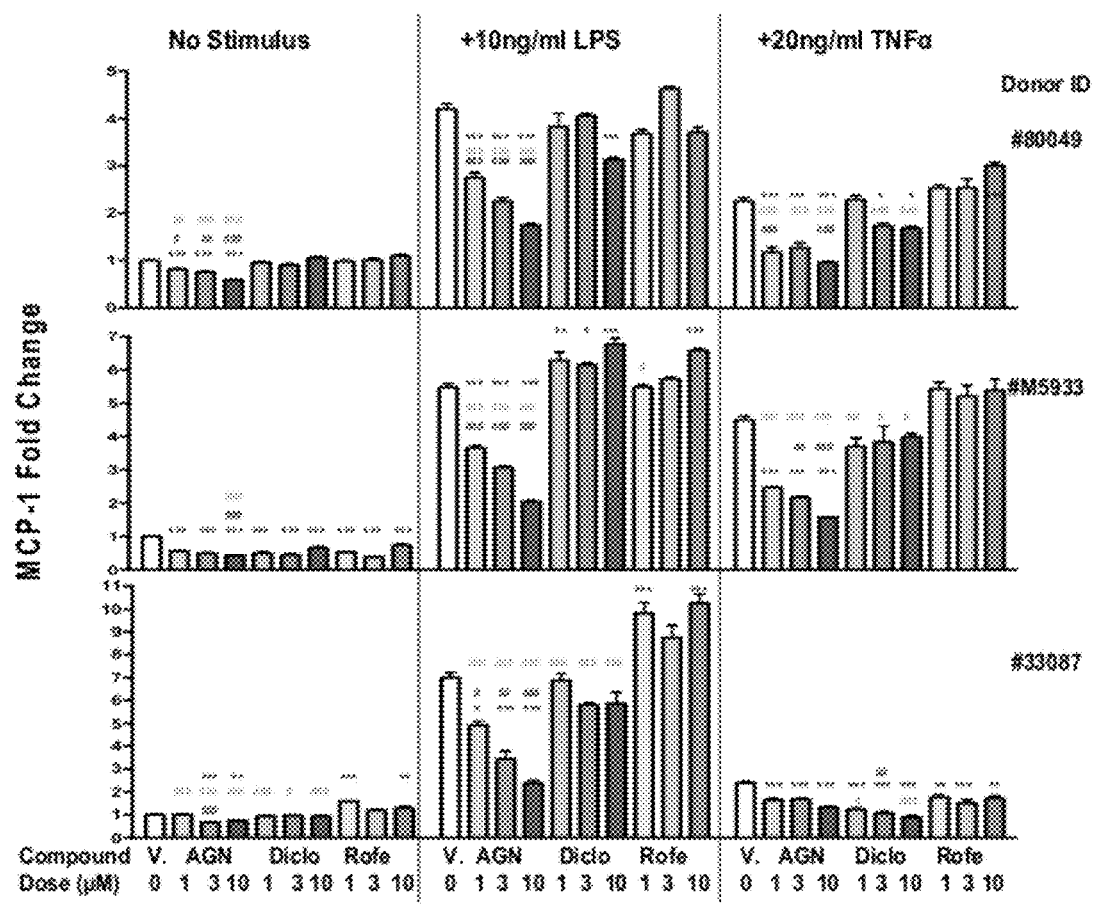
FIG. 3 shows a comparison of this representative compound of this invention with diclofenac and rofecoxib in modulating the secretion of MCP-1 from human macrophages stimulated by LPS and TNFα (n=three donors, normalized by cell viability)
Figure 4:
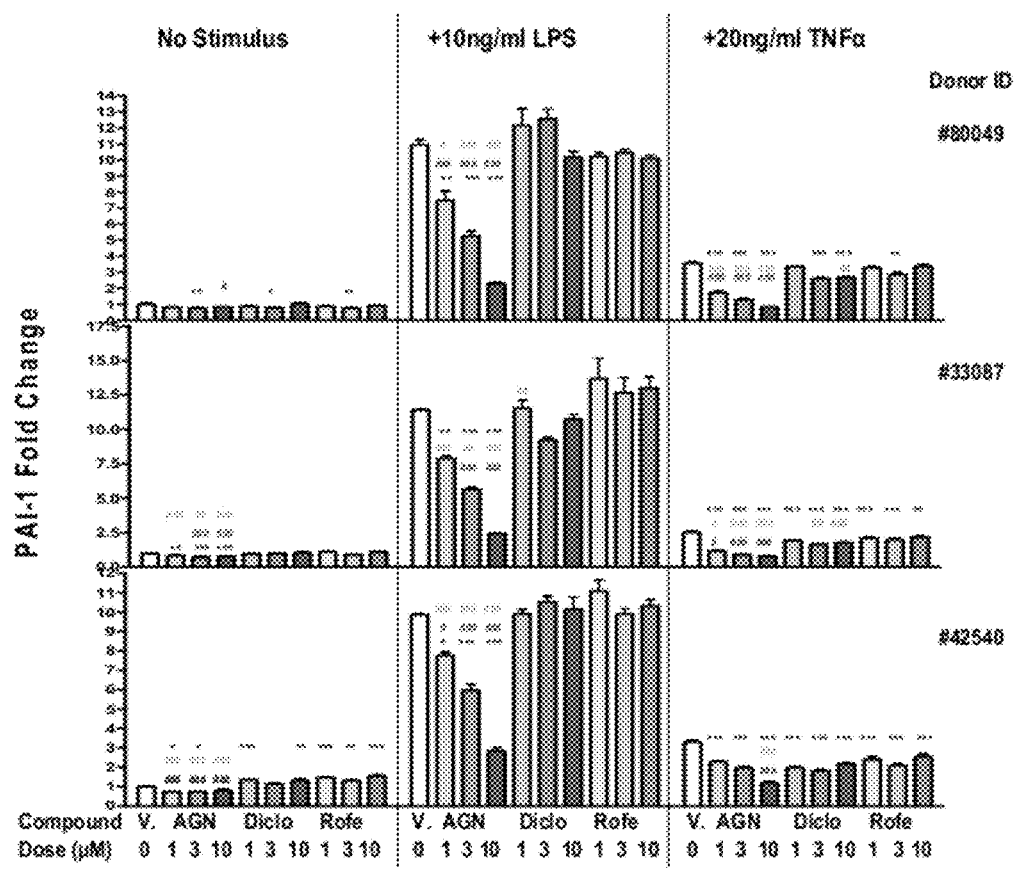
FIG. 4 shows a comparison of this representative compound of this invention with diclofenac and rofecoxib in modulating the secretion of PAI-1 from human macrophages stimulated by LPS and TNFα (n=three donors, normalized by cell viability)
Figure 5:
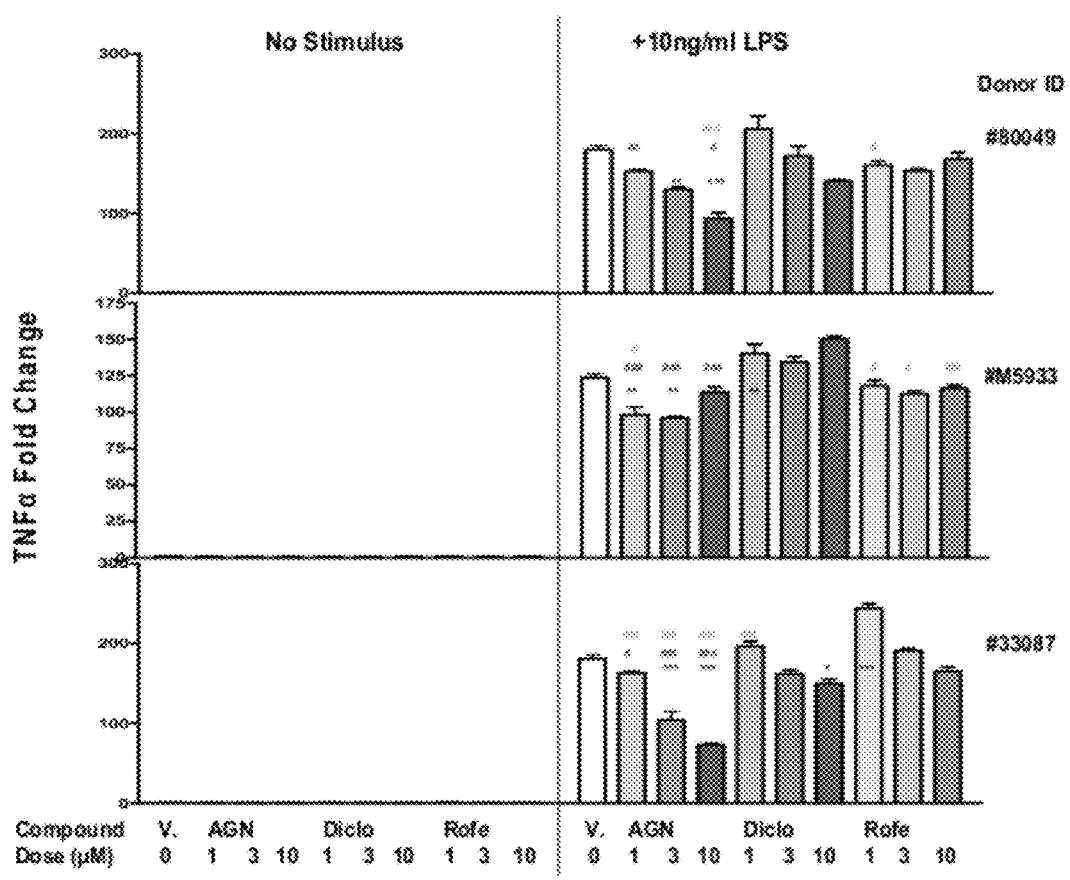
FIG. 5 shows a comparison of this representative compound of this invention with diclofenac and rofecoxib in modulating the secretion of TNFα from human macrophages stimulated by LPS (n=three donors, normalized by cell viability)
Figure 6:
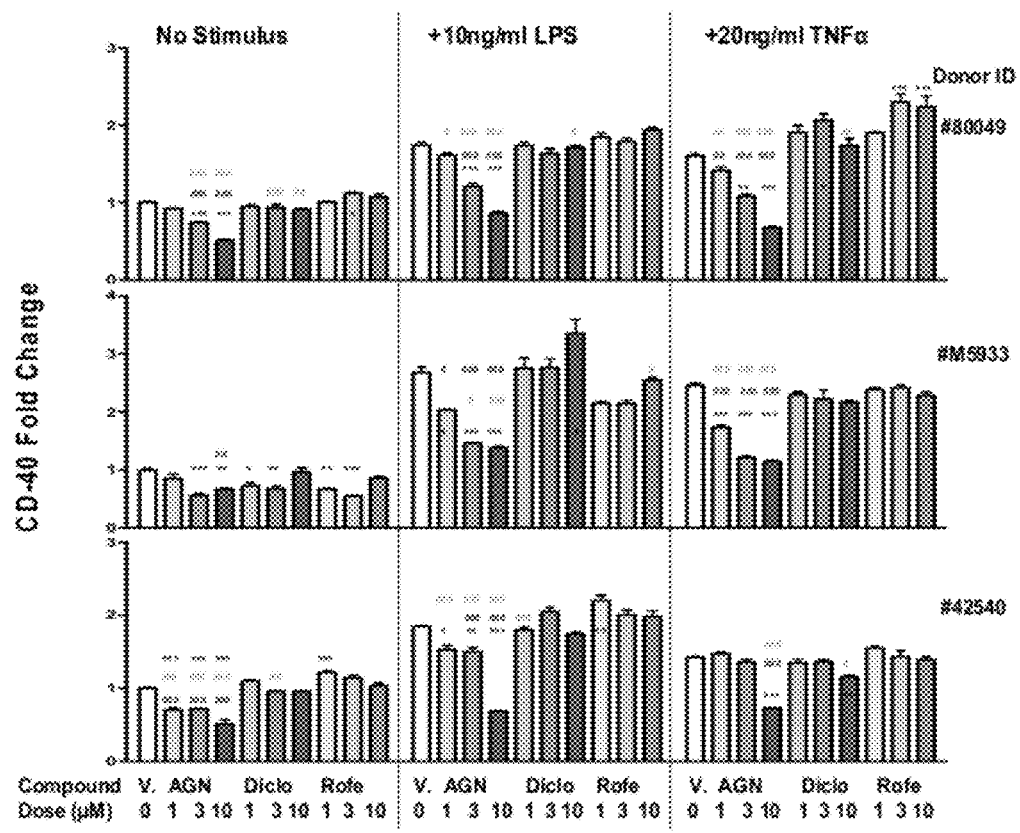
FIG. 6 shows the results a comparison of this representative compound of formula I, diclofenac, and rofecoxib on CD-40 secretion from human macrophages stimulated by LPS and TNFα (n=three donors, normalized by cell viability)
Figure 7:
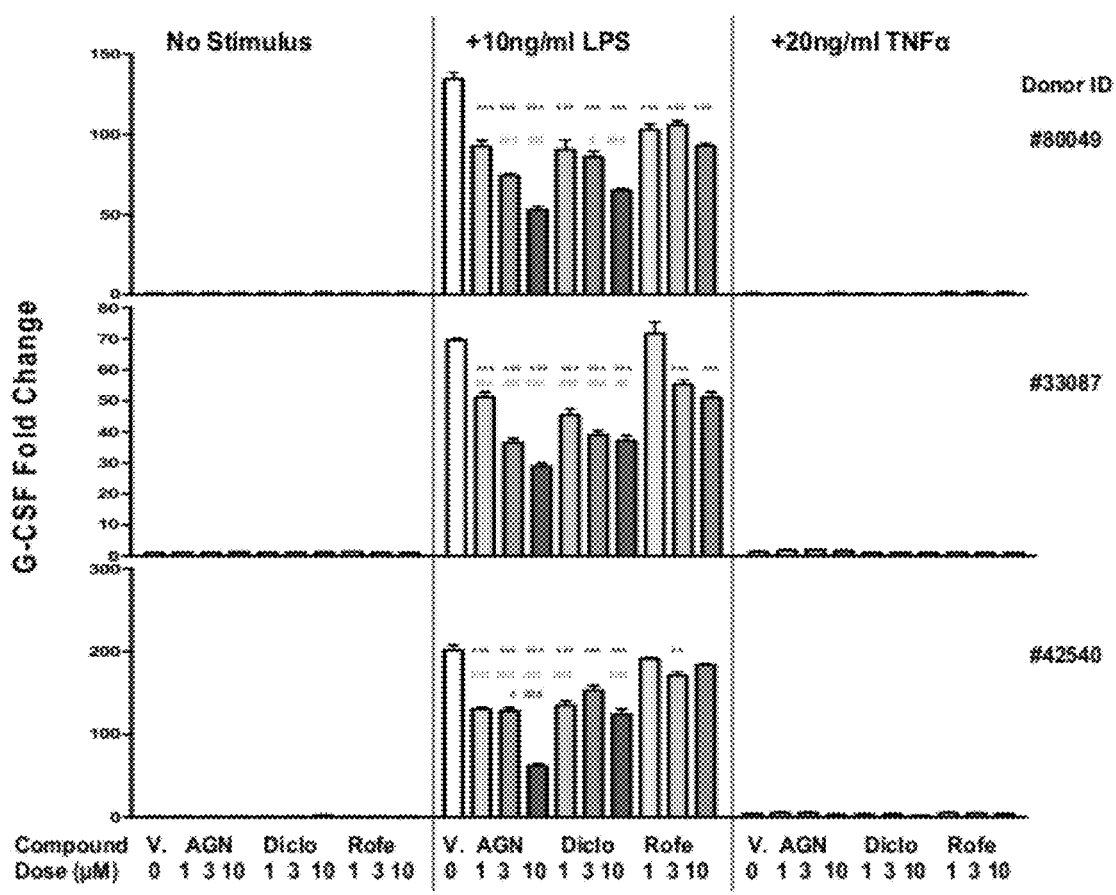
FIG. 7 shows the results a comparison of this representative compound of formula I, diclofenac, and rofecoxib on G-CSF secretion from human macrophages stimulated by LPS and TNFα (n=three donors, normalized by cell viability)
Figure 8:
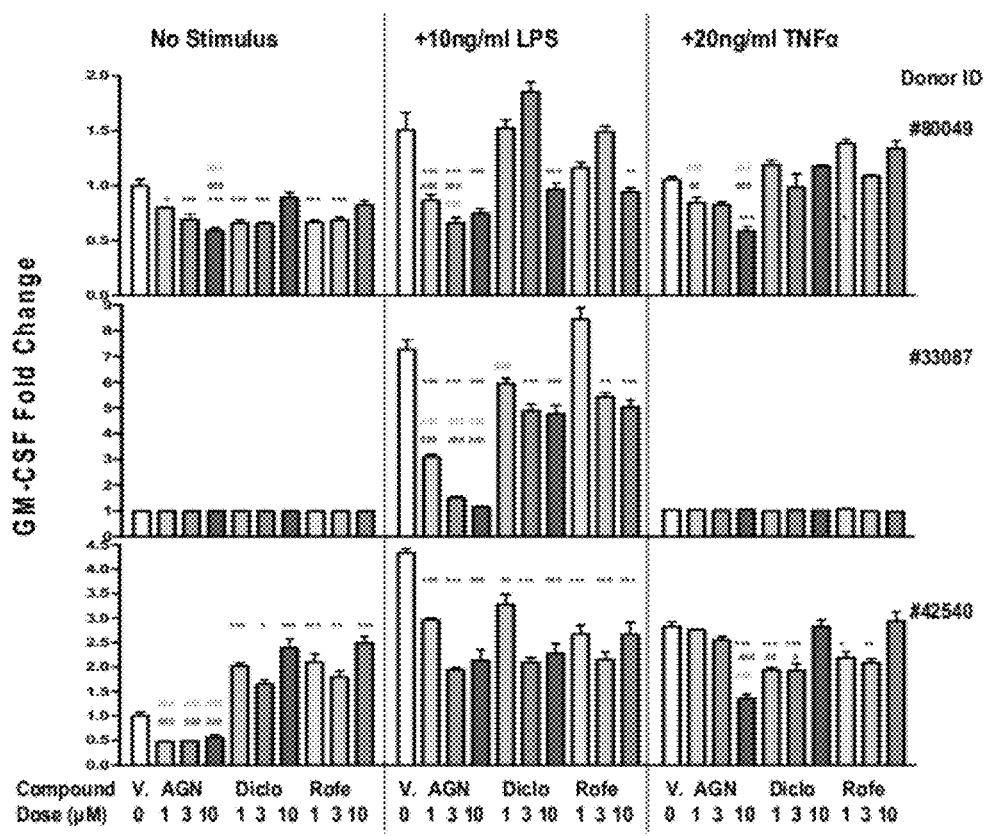
FIG. 8 shows the results a comparison of this representative compound of formula I, diclofenac, and rofecoxib on GM-CSF secretion from human macrophages stimulated by LPS and TNFα (n=three donors, normalized by cell viability)
Figure 9:
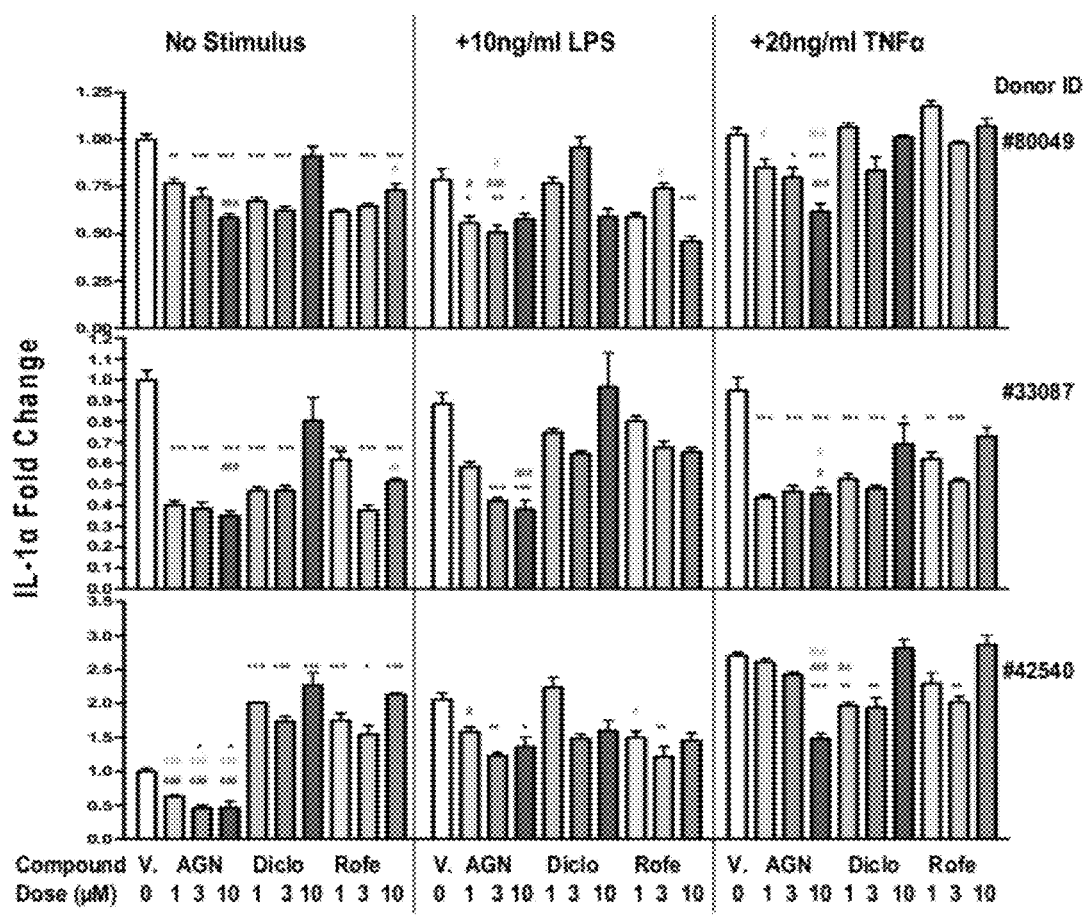
FIG. 9 shows the results a comparison of this representative compound of formula I, diclofenac, and rofecoxib on IL-1α secretion from human macrophages stimulated by LPS and TNFα (n=three donors, normalized by cell viability)
Figure 10:
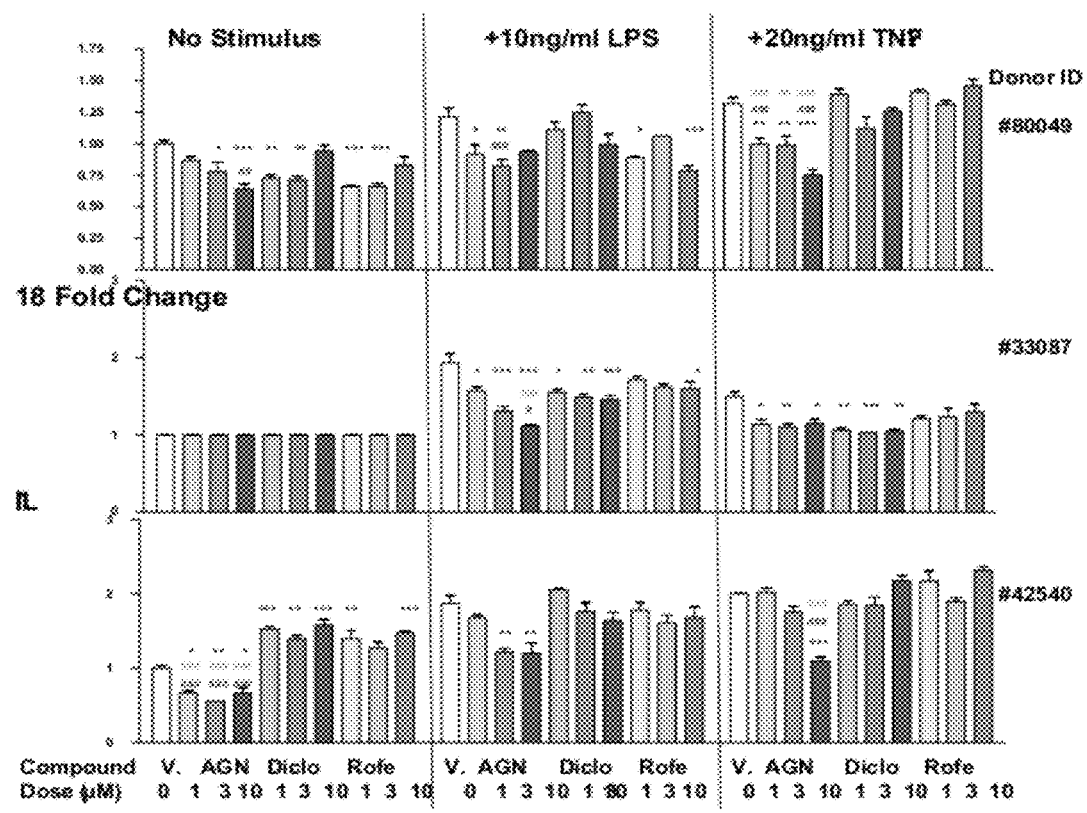
FIG. 10 shows the results a comparison of this representative compound of formula I, diclofenac, and rofecoxib on IL-18 secretion from human macrophages stimulated by LPS and TNFα (n=three donors, normalized by cell viability)
Figure 11:
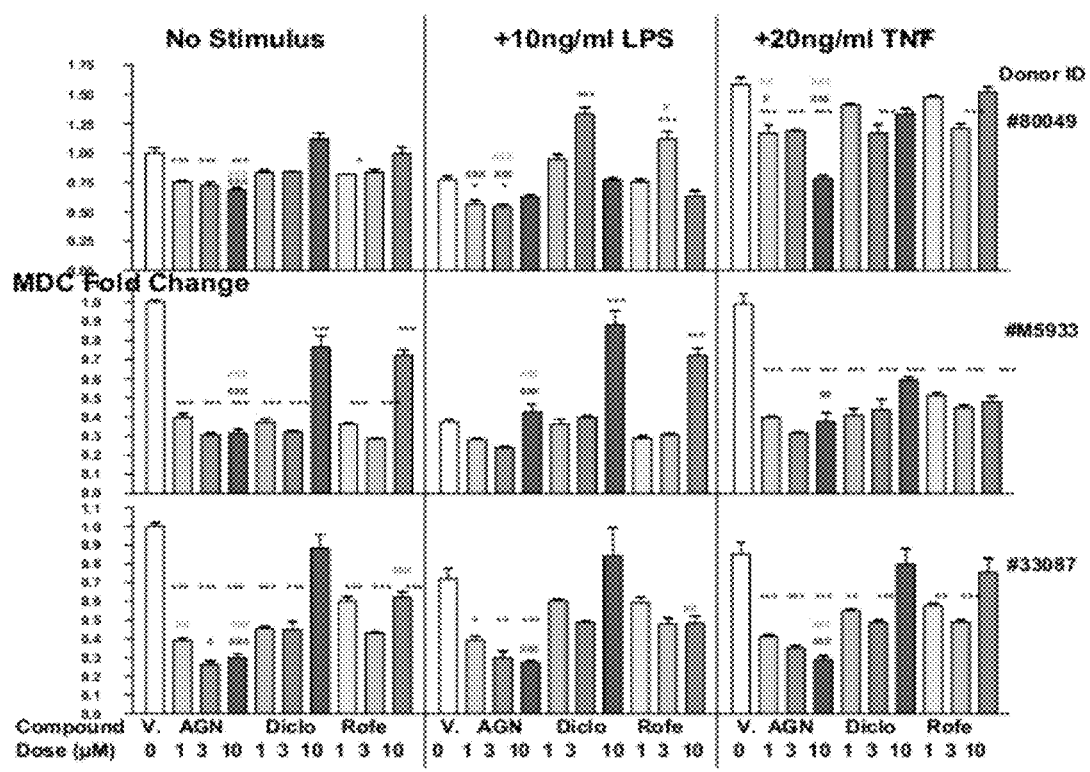
FIG. 11 shows the results a comparison of this representative compound of formula I, diclofenac, and rofecoxib on MDC secretion from human macrophages stimulated by LPS and TNFα (n=three donors, normalized by cell viability)
Figure 12:
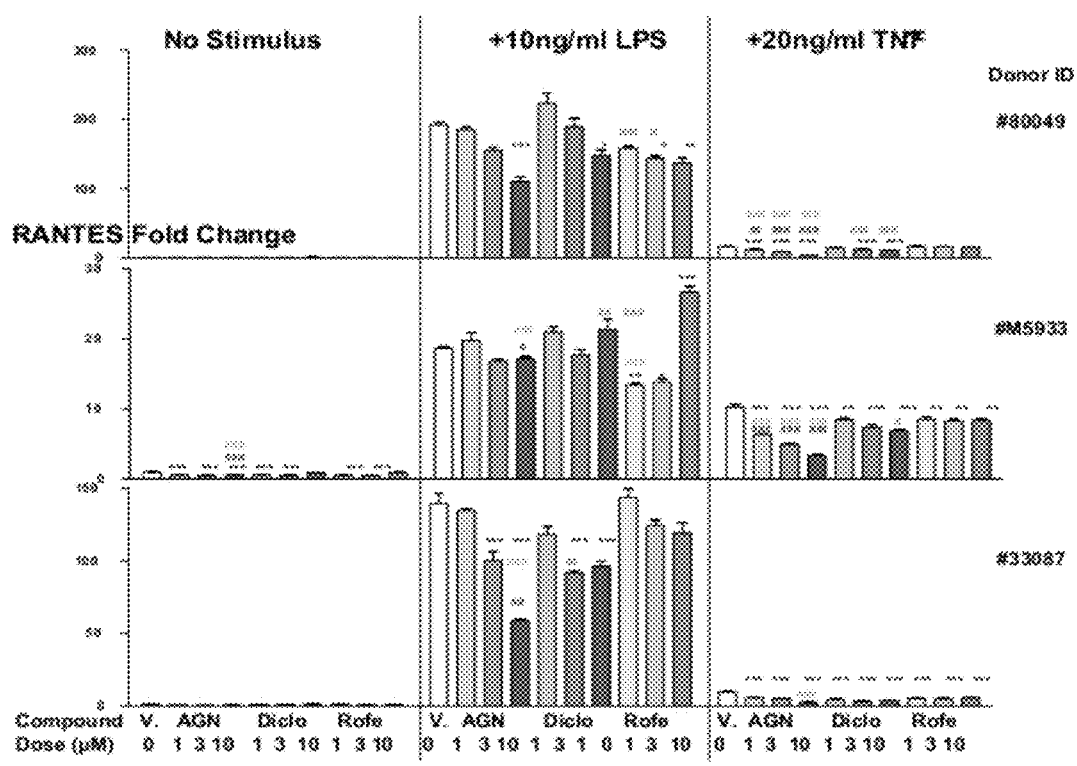
FIG. 12 shows the results a comparison of this representative compound of formula I, diclofenac, and rofecoxib on RANTES secretion from human macrophages stimulated by LPS and TNFα (n=three donors, normalized by cell viability)

Accordingly, the present invention relates to a method of treating inflammation resulting from inflammatory diseases characterized by monocytic infiltration caused by the secretion of cytokines and/or chemokines by administration, to a patient in need of said treatment, of a pharmaceutical composition comprising a compound represented by the general formula:

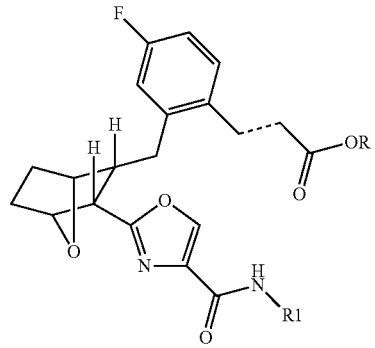

wherein R is H or lower alkyl, R1 is hydrocarbyl or substituted hydrocarbyl and the broken line represents a saturated or unsaturated bond, i.e. a double bond, in an amount effective to decrease the secretion of cytokines and/or chemokines Preferably, R1 is an alkyl. More preferably, R1 is a n-alkyl or a cycloalkyl-n-alkyl, e.g. a cyclohexyl-n-alkyl, e.g. n-octyl, n-nonyl or cyclohexyl-n-butyl radical and prodrugs, isomers and pharmaceutically acceptable salts thereof. Most preferably, R1 is a cyclohexyl-n-butyl radical.

In the definition of the compound represented by the general formula:

"Pharmaceutically acceptable salt" refers to those salts which retain the biological effectiveness and properties of the free base and which are obtained by reaction with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like or retain the biological effectiveness and properties of the free acid and which are obtained by reaction with inorganic bases such as sodium and potassium hydroxides or carbonates, etc.

"Prodrug" refers to compounds that decompose under in-vivo conditions to yield the compound of formula I or a pharmaceutically acceptable salt thereof.

"Alkyl" refers to a straight-chain, branched or cyclic saturated aliphatic hydrocarbon. Preferably, the alkyl group has 1 to 12 carbons. More preferably, it is an alkyl of from 4 to 10 carbons, most preferably 4 to 8 carbons. Typical alkyl groups include methyl, ethyl, propyl, isopropyl, butyl, isobutyl, tertiary butyl, pentyl, hexyl and the like. The alkyl group may be optionally substituted with one or more substituents are selected from the group consisting of hydroxyl, cyano, alkoxy, =O, =S, $NO_2$, halogen, dimethyl amino, and SH.

"Cycloalkyl" refers to a cyclic saturated aliphatic hydrocarbon group. Preferably, the cycloalkyl group has 3 to 12 carbons. More preferably, it has from 4 to 7 carbons, most preferably 5 or 6 carbons.

The compounds of the invention have the basic profile of a safer COXIB replacement with minimal cardiovascular liability and renal toxicity, wherein prostanoid $DP_1$, $EP_1$, $EP_4$, FP, and TP receptors were blocked, $DP_2$ receptors were partially blocked, while leaving $EP_2$ receptors open, and having no antagonizing activity at IP receptors crucial for cardiovascular safety, and very little activity at $EP_3$ receptors important for GI tract and renal protection. Therefore, said compounds provide a novel approach for anti-inflammatory therapy. With this profile, it is hypothesized that the compounds utilized in the method of this invention, e.g. (E)-3-(2R-{3R-[4-(4-Cyclohexyl-butylcarbamoyl)-oxazol-2-yl]-7-oxa-bicyclo[2.2.1]hept-2-ylmethyl}-4-fluoro-phenyl)-acrylic acid would exhibit anti-inflammatory effects in two dimensions: (a) blocking proinflammatory PG effects via receptors $DP_1$, $EP_1$, $EP_4$, FP, and TP; (b) allowing $PGE_2$ to exert anti-inflammatory effects via $EP_2$ receptors. The unique pharmacological profile of (E)-3-(2R-{3R-[4-(4-Cyclohexyl-butylcarbamoyl)-oxazol-2-yl]-7-oxa-bicyclo[2.2.1]hept-2-ylmethyl}-4-fluoro-phenyl)-acrylic acid also identifies itself as a safer replacement for NSAIDs and COXIBs in two dimensions, (a) by allowing IP receptors to exert their function of lowering blood pressure and preventing platelet aggregation, and (b) by keeping $EP_3$ receptors open for normal renal function and GI tract cytoprotection. These features are advantageously different from just non-selectively inhibiting all PG production from both COX enzymes like the NSAIDs, or blocking all PG synthesized by COX-2 like the COXIBs.

The current finding that (E)-3-(2R-{3R-[4-(4 Alkylcarbamoyl)-oxazol-2-yl]-7-oxa-bicyclo[2.2.1]hept-2-ylmethyl}-4-fluoro-phenyl)-acrylic acid or propionic acid and alkyl esters thereof are effective in attenuating the production of TNF family cytokines (CD40 and TNFα), and the classical interleukin-1 (IL-1) family cytokines (IL-1α and IL-18) is especially important. These cytokines exert a broad spectrum of biological and pathological effects. They play key roles in inflammation and RA pathogenesis by stimulating the release of multiple proinflammatory cytokines, including themselves, through the NFκB signaling pathway. Certain antagonists/antibodies for IL-1 and IL-18 are currently under preclinical investigation for RA treatment, while the TNFα antibodies are already available for RA treatment. Although alleviating the symptoms of RA in 50-65% of patients, a TNFα antibody is very expensive to use compared to chemically synthesized small molecules, inconvenient to administer usually requiring injections, and has been linked to tuberculosis, lymphoma, and other adverse effects. Unlike a TNFα antibody that totally eliminates all circulating TNFα in the system, (E)-3-(2R-{3R-[4-(4-Alkylyl-carbamoyl)-oxazol-2-yl]-7-oxa-bicyclo[2.2.1]hept-2-yl methyl}-4-fluoro-phenyl)-acrylic acid or propionic acid and alkyl esters thereof only attenuates the production of TNFα by inhibiting proinflammatory PG receptors. Therefore the adverse effects associated with a TNFα antibody in elevating infectious and cancerous tendency is less likely.

Finally, the current finding that (E)-3-(2R-{3R-[4-(4-Alkylcarbamoyl)-oxazol-2-yl]-7-oxa-bicyclo[2.2.1]hept-2-ylmethyl}-4-fluoro-phenyl)-acrylic acid or propionic acid or the alkyl esters thereof inhibit PAI-1 production in human macrophages is important in cardiovascular and metabolic pathological conditions. In addition to PAI-1, other biomarkers inhibited by (E)-3-(2R-{3R-[4-(4-Alkylcarbamoyl)-oxazol-2-yl]-7-oxa-bicyclo[2.2.1]hept-2-yl and methyl}-4-fluoro-phenyl)-acrylic acid or propionic acid and alkyl esters thereof that are known to be closely related to inflammatory conditions, have also been implicated in thrombosis and atherosclerosis. Cells capable of forming atherosclerotic plaque include monocytes, macrophages, endothelial cells, smooth muscle cells, platelets and T cells. These cells express CD40 receptors, and release CD40 ligand (CD40L) upon thrombin stimulation. MDC secreted by monocytes and macrophages has been shown to be a strong and rapid activator of platelet aggregation and adhesion. Proinflammatory elements IL-1, TNF, RANTES, and MCP-1 are also involved in the cascade of events in the early and late stages of atherosclerosis. Plasma MCP-1 levels have been linked to cardiovascular disease risk factors in clinical studies. Platelet activation leads to the release of MIP-1α, RANTES, ENA-78, and IL-8, which attract leukocytes and further activate other platelets. These evidences provide a direct linkage between homeostasis, infection, and inflammation and the development of atherosclerosis. (E)-3-(2R-{3R-[4-(4-Alkylcarbamoyl)-oxazol-2-yl]-7-oxa-bicyclo[2.2.1]hept-2-ylmethyl}-4-fluoro-phenyl)-acrylic acid and propionic acid and alkyl esters thereof is able to target multiple biomarkers of inflammation, thrombosis, and atherothrombosis simultaneously, which may confer pharmaceutical potential on (E)-3-(2R-{3R-[4-(4-Alkylcarbamoyl)-oxazol-2-yl]-7-oxa-bicyclo[2.2.1]hept-2-yl methyl}-4-fluoro-phenyl)-acrylic acid and propionic acid and alkyl esters thereof in treating atherosclerosis and atherothrombosis. As a result, (E)-3-(2R-{3R-[4-(4-Alkylcarbamoyl)-oxazol-2-yl]-7-oxa-bicyclo[2.2.1]hept-2-ylmethyl}-4-fluoro-phenyl)-acrylic acid and propionic acid and alkyl esters thereof is unlikely to be associated with cardiovascular liability as in the case of the COXIBs, conversely it may even have a beneficial effect on cardiovascular function.

In summary, because of their ability to suppress the synthesis of some key proinflammatory cytokines/chemokines CD40, ENA-78, G-CSF, GM-CSF, IL-1α, IL-8, IL-18, MCP-1, MDC, RANTES, and TNFα, as well as the adipocytokine PAI-1, the compounds of FORMULA 1 are not only at least as effective as COXIBs and NSAIDs in RA treatment, but also are a safer therapy in RA treatment. They are also be a potential therapy for cardiovascular diseases.

The compounds of this invention treat or prevent inflammation at least in part by the decreasing the amount of the secretion of certain cytokines and/or chemokines that result from the exposure of the patient to a stimulant.

In particular, the secretion of IL-8, ENA-7, MCP-1, PAI-1, TNFα, CD-40, G-CSF, GM-CSF, IL-1α, IL-18, MDC, and RANTES is reduced in those instances where said secretions are triggered by lipopolysaccharides (LPS) and or TNFα.

The compounds of the present invention can be administered orally or parenterally. The dosage is 3 to 150 mg/kg per day for an oral administration and 1 to 50 mg/kg per day for a parenteral administration.

When the compound is administered as a pharmaceutical, it can be prepared using usual formulation techniques and used in a dosage form of solid or liquid, such as tablets, capsules, powders, granules, suppositories, solution, suspension or emulsion.

Further, in this case, additive components which are customarily used for pharmaceutical preparations such as excipients, disintegrators, lubricants, binders, preservatives, stabilizers, osmotic pressure regulating agents and so forth can be used.

An example of these additive components include, glucose, lactose, starches, carboxymethylcellulose, magnesium stearate, talc, liquid paraffin, polyvinyl alcohol, vegetable oil, polyalkylene glycol and so forth. Other pharmaceutical ingredients can be also included.

The preparation of the compound of the present invention will be described below in more details based on the Examples. The Examples evaluate the effect of the compounds of this invention on the following biological entities and are predictive of the effect of the present compounds in treating diseases and conditions associated with said biological entities.

Epithelial neutrophil-activating protein 78 (ENA-78, or CXCL5) and Interleukin-8 (IL-8, or CXCL8): function as potent chemoattractants and activators of neutrophils, ENA-78 and IL-8 are produced concomitantly in response to stimulation with either IL-1 or TNFα. They not only account for a significant proportion of the chemotactic activity for neutrophils in rheumatoid arthritis (RA) synovial fluids, but also are potent angiogenic factors in the RA synovium.

Monocyte chemoattractant protein-1 (MCP-1, or CCL-2): is not only believed to play a role in inflammatory diseases characterized by monocytic infiltration, such as RA rheumatoid arthritus, psoriasis, and atherosclerosis, but is also implicated in other diseases, such as atopic dermatitis, renal disease, pleurisy, allergy and asthma, colitis, endometriosis, polymyositis and dermatomyositis, uveitis, restenosis, brain inflammation and obesity. MCP-1 also controls leukocyte trafficking in vascular cells involved in diabetes and diabetes-induced atherosclerosis. MCP-1 antibodies are potential therapeutic agents for treating MCP-1/CCR2-mediated multiple inflammatory diseases.

Plasminogen activator inhibitor 1 (PAI-1) is a potent inhibitor of plasminogen fibrinolysis. In addition to inhibiting fibrinolysis, PAI-1 also plays an important role in regulating cell proliferation, adhesion, migration, and apoptosis of vascular smooth muscle cells and endothelial cells. TNFα elevates both local and plasma concentrations of PAI-1, which results in excessive fibrin accumulation, and the sequential luminal obstruction, thrombus formation, atherosclerotic lesions, vascular inflammation, and pathological evolution of atherosclerotic plaques. Increase levels of PAI-1 have been associated with pathological conditions, including deep vein thrombosis, atherosclerosis, renal and pulmonary fibrosis, and cancer; as well as metabolic syndrome with a combination of obesity, insulin resistance, hypertension, and hypertriglyceridemia, which will eventually develop into type 2 diabetes and atherothrombosis. Judging from the fact that several currently available renal protective drugs have PAI-1 inhibitory activity, PAI-1 also plays a key role in renal fibrosis. Therefore, abnormal PAI-1 expression may is a useful therapeutic target for renal and cardiovascular diseases.

Tumor necrosis factor α (TNFα): mainly secreted by macrophages and recognized for its importance in activating the cytokine cascade. TNFα stimulates the production of proinflammatory cytokines/chemokines, collagenases, metalloproteinases, and other inflammatory mediators; activates endothelial cells and neutrophils; promotes T- and B-cell growth, as well as stimulating bone resorption. The TNFα antibody infliximab not only decreases the production of local and systemic proinflammatory cytokines/chemokines, but also reduces serum MMP-3 production, nitric oxide synthase activity, VEGF release, and angiogenesis in inflamed joints.

CD40 signaling include regulation of antibody production by B cells, induction of T cell proliferation, and activation of antigen-presenting cells, such as dendritic cells (Rizvi et al., 2008). In monocytes/macrophages, binding of the CD40L induces the multimerization of CD40 receptors and activation of the TNF receptor-associated factor (TRAF) pathway. Proinflammatory cytokines/chemokines, such as IL-1α/β, IL-8, MIP-1α, and TNFα, are released as the result of CD40-CD40L interaction. A polymorphism in the CD40 locus is associated with the rate of joint destruction in patients with RA (van der Linden et al., 2009), and a strong association of the CD40 gene with RA has been confirmed in a large UK case-control study (Orozco et al., 2009). CD40 is also present in cells involved in atherosclerosis, including macrophages, endothelial cells and vascular smooth muscle cells (Rizvi et al., 2008). The interaction between CD40 and CD40L triggers platelet activation, which is crucial for inflammation, thrombosis and atherosclerosis (Rizvi et al., 2008). The soluble form of CD40, which is detected in the culture media of human macrophages in the current study, is presumably produced by shedding from membrane-bound CD40 (Schwabe et al., 1999). Soluble CD40 levels are observed to be elevated in the serum of patients with chronic renal failure (Schwabe et al., 1999), chronic liver diseases (Schmilovitz-Weiss et al., 2004), Alzheimer's disease (Mocali et al., 2004), and systemic sclerosis—an autoimmune disease (Komura et al., 2007).

Granulocyte colony-stimulating factor (G-CSF) is a major regulator of neutrophil production and survival. G-CSF, along with Granulocyte-macrophage colony-stimulating factor (GM-CSF), were the first cytokines found in RA synovial fluid and synovium. The normally very low serum levels of G-CSF rise dramatically during bacterial infection and fall rapidly with resolution of infection. The elevation of serum levels of G-CSF also correlate with disease activity of RA (Cornish et al., 2009). G-CSF treatment can exacerbate underlying inflammatory diseases in humans and mice, and G-CSF deficiency in collagen-induced arthritic mice has profound protective effects. These findings suggest that G-CSF is an important proinflammatory cytokine (Eyles et al., 2006). Granulocyte-macrophage colony-stimulating factor (GM-CSF) is produced by a variety of cell types, including activated T cells and macrophages. Production of GM-CSF can be stimulated by lipopolysaccharide (LPS), tumor necrosis factor (TNF), and IL-1 (Cornish et al., 2009). While G-CSF is largely neutrophil specific, GM-CSF stimulates the growth and differentiation of neutrophils, macrophages, dendritic cells, eosinophils, and erythrocytes [(Cornish et al., 2009). In addition to the colony-stimulating effects on bone-marrow progenitor cells, a major role for both G-CSF and GM-CSF is to enhance the production of mediators by mature neutrophils and macrophages. Both G-CSF and GM-CSF are found in the joints of RA patients. Administration of both cytokines exacerbates RA, and antagonism of G-CSF or GM-CSF markedly reduces established disease in mouse RA models. Biologic-based antagonists of both G-CSF and GM-CSF are currently being developed and evaluated for RA therapy (Cornish et al., 2009).

Interleukin-1α (IL-1α) and Interleukin-1β (IL-1β) play an important role in immune regulation and inflammatory processes by inducing nitric oxide synthase and matrix metalloproteinases, as well as proinflammatory cytokines/chemokines (Barksby et al., 2007) including TNFα, IL-8, ENA-78, MCP-1, MIP-1α, and MIP-1β (St. Clair et al., 2004). Produced by synovial tissue macrophages, activated T cells, fibroblasts and chondrocytes, IL-1β is elevated in synovial fluids from RA patients and results in the local effects of increased leukocyte infiltration and MMP-mediated tissue turnover (Barksby et al., 2007). IL-1 cytokines are key immune mediators responsible in inflammation and tissue destruction in RA, and are detected after the early stages of RA (Barksby et al., 2007). Clinical studies indicate that the recombinant human IL-1 receptor antagonist Anakinra is a safe and well tolerated therapy for long-term use in RA (Barksby et al., 2007).

Interleukin-18 (IL-18) is a cytokine that also belongs to the IL-1 family. IL-18 is important in both innate and acquired immune responses. It stimulates neutrophil migration/activation and T helper 1 (Th1) cell differentiation, as well interferon IFN-γ secretion in T lymphocytes and NK cells (Barksby et al., 2007). In RA, IL-18, spontaneously and mainly released from macrophages, activates T cells and macrophages to produce proinflammatory cytokines/chemokines, adhesion molecules and RANKL to perpetuate chronic inflammation and induce bone and cartilage destruction (Dai et al., 2007). IL18 upregulates IL-8, MCP-1, VEGF, and particularly TNFα. TNFα, in turn, increases IL-18 expression in RA synovial cells (Matsui et al., 2003). Therefore, IL-18 plays a critical role and is a potential therapeutic target in RA. Currently, anti-IL-18 therapies are ongoing at the preclinical trial stage (Barksby et al., 2007).

Macrophage-derived chemokine (MDC) induces chemotaxis for monocyte-derived dendritic cells, activated T cells and natural killer (NK) cells (Ho et al., 2003). Highly expressed by the three major cell types involved in allergic inflammation: eosinophils, basophils, and Th2 lymphocytes (Garcia et al., 2005), as well as highly expressed in atopic dermatitis (Pivarcsi et al., 2005), MDC plays a role in inflammatory diseases such as allergic asthma and atopic dermatitis (Ho et al., 2003). Significantly enhanced in keratinocytes of patients with atopic dermatitis, MDC could be a candidate therapeutic target for inflammatory skin disease such as atopic dermatitis (Qi et al., 2009). MDC is also implicated in disease activity of RA. After combination treatment with the disease-modifying anti-rheumatic drugs leflunomide and methotrexate in RA patients, plasma MCP-1 and MDC concentrations were significantly lower, and so was the recruitment of inflammatory cells into the sites of inflammation (Ho et al., 2003). Moreover, MDC also amplify platelet activation and has been associated with the pathogenesis of atherosclerotic disease including thrombosis (Gleissner et al., 2008).

Regulated on Activation, Normal T Cell Expressed and Secreted (RANTES) is a chemoattractant for blood monocytes, memory T-helper cells and eosinophils, and plays an active role in recruiting leukocytes into inflammatory sites. It also stimulates the release of histamine from basophils, activates eosinophils and causes hypodense eosinophils, which is associated with diseases such as asthma and allergic rhinitis. RANTES receptor CCR5 is also expressed on cells involved in atherosclerosis (e.g. monocytes/macrophages, T lymphocytes, or Th1-type cells), and is specialized in mediating RANTES-triggered atherosclerotic plaque formation (Zernecke et al., 2008). Like MCP-1, stimulation with RANTES enhances production of IL-6 and IL-8 in RA fibroblast-like synovial cells; elevated MMP-3 production by chondrocytes, and inhibited proteoglycan synthesis and enhanced proteoglycan release from the chondrocytes (Iwamoto et al., 2008). Both MCP-1 and RANTES were found to play an important role in allergic lung inflammation, lung leukocyte infiltration, bronchial hyper-responsiveness, and the recruitment of eosinophils in the pathogenesis of asthma (Conti et al., 2001). Similar to MCP-1, RANTES also enhances the inflammatory response within the nervous system, which plays an apparent role in the pathogenesis of multiple sclerosis (Conti et al., 2001) Inhibitors for RANTES may provide clinical benefits in treating inflammation, CNS disorders, parasitic disease, cancer, autoimmune and heart diseases (Castellani et al., 2007).

Certain of the compounds utilized in the pharmaceutical compositions and methods of treatment of the present invention are prepared as shown in the following examples which examples are not intended to be limiting but are preferred embodiments of the invention.

EXAMPLE 1

(E)-3-(2R-{3R-[4-(4-Cyclohexyl-butylcarbamoyl)-oxazol-2-yl]-7-oxa-bicyclo[2.2.1]hept-2-ylmethyl}-4-fluoro-phenyl)-acrylic acid

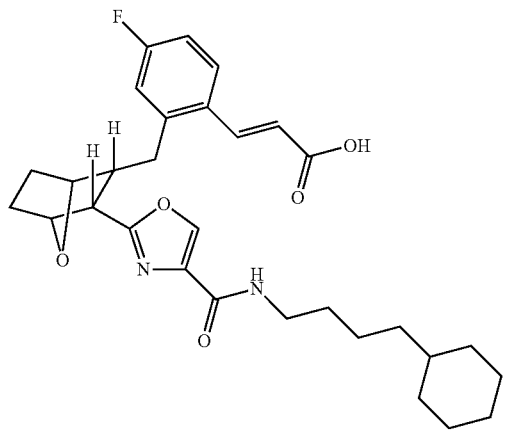 [SMILES: O=C(O)/C=C/c1ccc(F)cc1CC1C2CCC(O2)C1c1nc(C(=O)NCCCCC2CCCCC2)co1]

Step 1

(4R,5R)-2-(2-Bromo-4-fluoro-phenyl)-3,4-dimethyl-5-phenyl-oxazolidine

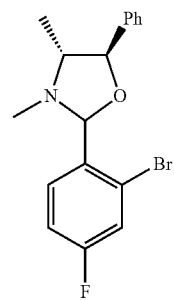 [SMILES: C[C@@H]1[C@@H](c2ccccc2)OC(c2ccc(F)cc2Br)N1C]

To a solution 2-bromo-4-fluorobenzaldehyde (15.2 g, 74.9 mmol) in toluene (80 ml) was added (1R,2R)-(−)-pseudoephedrine (13.6 g, 82 mmol) and the resulting mixture was refluxed removing water using a Dean-Stark trap for 16 h. The reaction was halted and cooled down to room temperature. The solution was washed with citric acid solution (1M, 100 ml), saturated sodium bicarbonate solution (50 ml), brine (50 ml) and dried ($MgSO_4$). Then, it was filtered and the solvent was evaporated under vacuum to give title compound as yellow oil. (26.2, yield=97%).

$^1$H-NMR ($CDCl_3$, 300 MHz) 7.78 (dd, 1H, J=5.7, 8.6 Hz, ArH), 7.36 (m, 6H, ArH), 7.11 (m, 1H, ArH), 5.47 (s, 1H,

—N—CH—O—), 4.71 (d, 1H, J=8.64 Hz, —CH-Ph), 2.60 (m, 1H, —CH—CH₃), 2.27 (s, 3H, —CHCH₃). ¹⁹F-NMR (CDCl₃, 300 MHz) γ −111.6

Step 2γ

4-Fluoro-2-(5-oxo-4,10-dioxa-tricyclo[5,2R,1R,0*2,6*]dec-3S-yl)-benzaldehyde

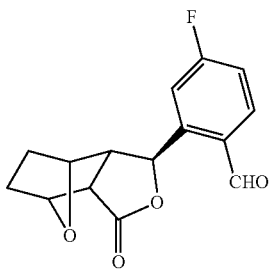 [SMILES: O=Cc1ccc(F)cc1[C@H]1OC(=O)C2C3CCC(O3)C21]

To a stirred solution of (4R,5R)-2-(2-Bromo-4-fluoro-phenyl)-3,4-dimethyl-5-phenyl-oxazolidine 22 (25.5 g, 72.8 mmol) in anhydrous THF (50 mL) at −78° C. and under nitrogen atmosphere, was added slowly n-Butyl lithium 1.6M (32.9 ml, 82.2 mmol) keeping the internal temperature below −60° C. The resulting mixture was stirred for 10 minutes at −78° C., warmed up to −60° C. and stirred for 4 h.

At the same time, in a separate three neck 1 litre round bottle equipped with A condenser, dropping funnel and under A nitrogen atmosphere, 1,2-dibromoethane (7.95 ml, 92.2 mmol) was added slowly to a stirred suspension of magnesium (2.15 g, 92.2 mmol) in anhydrous THF (30 mL) maintaining constant reflux. Once the fizzing had stopped, anhydrous THF (100 ml) was added to suspend the white solid MgBr₂ and the suspension was cooled down to −60° C. To this cooled suspension, the lithium salt solution prepared above was added by canula. The resulting mixture was warmed up to −15° C. and stirred for 30 minutes. Then, it was cooled down to −60° C. and a solution of norcantharidin (13.8 g, 82.2 mmol) in anhydrous THF (50 ml) was added dropwise over 15 minutes and the resulting solution was stirred for 30 minutes. After this time the mixture was warmed up to −30° C. and stirred for 2.5 h. Then the mixture was cooled down to −60° C. and quenched with methanol (100 ml), followed by portion wise addition of sodium borohydride (3.9 g, 101.9 mmol). The mixture wasallowed to warm up to −25° C. and stirred for 1.5 h. A solution of hydrochloric acid (2M, 150 ml) was carefully added, the mixture was warmed up to room temperature and stirred for 14 h. The reaction mixture was concentrated in vacuo diluted with water (100 ml) and extracted with EtOAc (2×150 ml). The combined extracts were washed with brine (70 ml), dried over MgSO₄, filtered and the solvent was evaporated under vacuum to give crude product as a green solid (19.5 g). The crude product was purified by recrystallization from THF/isohexane (5:1) to yield the title compound as a white solid (10.1 g, yield=50%).

¹H-NMR (CDCl₃, 300 MHz) Y 10.05 (s, 1H, —CHO), 7.91 (dd, 1H, J=5.7, 8.6 Hz, ArH), 7.24 (m, 2H, ArH), 6.10 (d, 1H, J=3.1 Hz, —O—CH—Ar), 5.40 (m, 1H, —CH—O—), 4.97 (m, 1H, —CH—O), 2.87 (d, 1H, J=8.2 Hz, —CH—CO—), 2.28 (d, 1H, J=2.9, 8.2 Hz, —CH—), 1.84 (m, 2H, —CH₂—CH—), 1.55-1.44 (m, 2H, —CH₂—CH₂—). ¹⁹F-NMR (CDCl₃, 300 MHz) Y −110.6

Step 3

3R-(5-Fluoro-2-hydroxymethyl-benzyl)-7-oxa-bicyclo[2.2.1]heptane-2R-carboxylic acid

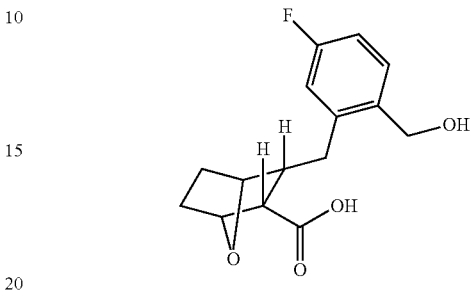

A solution of 4-Fluoro-2-(5-oxo-4,10-dioxa-tricyclo[5,2R,1R,0*2,6*]dec-3S-yl)-benzaldehyde (20 g, 71.9 mmol) and Pd on alumina (10% reduced, 4 g) in ethanol (1000 ml) was stirred at RT under hydrogen atmosphere for 30 min. The reaction mixture was filtered through celite and concentrated in vacuo, redissolved in ethanol (1000 ml) and Pd on alumina (10% reduced, 4 g) was added. The mixture was stirred at RT under a hydrogen atmosphere for another 30 min, filtered through celite and concentrated in vacuo to yield the title compound as a white solid, (20 g, 99%). ¹H-NMR (CDCl₃, 300 MHz) Y 7.41 (m, 1H, ArH), 7.01 (m, 2H, ArH), 4.65 (s, 1H, —CH—O—), 4.46 (s, 2H, —O—CH₂—Ar), 4.01 (m, 1H, —CH—O—), 2.79 (d, 1H, —CHCO₂), 2.64-2.31 (m, 3H, —CHCH—O and —CH₂—Ar), 1.61-1.24 (m, 4H, —CH₂— and —CH₂—). ¹⁹F-NMR (CDCl₃, 300 MHz) Y −116.7.

LC-MS: m/z 281 M+H⁺

Step 4

3R-(5-Fluoro-2-formyl-benzyl)-7-oxa-bicyclo[2.2.1]heptane-2R-carboxylic acid

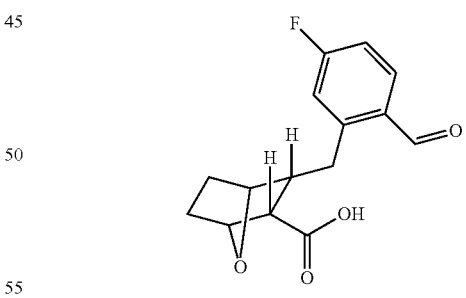

To a solution of 3R-(5-Fluoro-2-hydroxymethyl-benzyl)-7-oxa-bicyclo[2.2.1]heptane-2R-carboxylic acid (20 g, 71 mmol) in refluxing DCE (700 mL) was added activated MnO₂ (67 g ml, 655 mmol) in 10 equal portions within 5 hours. Methanol (50 ml) was added, the mixture was allowed to cool to rt, filtered through a silica plug (2 cm), the solids were washed with isopropanol:MeOH (1:1, 1000 ml) and concentrated in vacuo to yield the title compound as a light brown solid (17.7 g, 90%).

LC-MS: m/z 279 M+H⁺. The aldehyde was used without further purification in thesubsequent step.

Step 5

3R-[5-Fluoro-2-(2-methoxycarbonyl-vinyl)-benzyl]-7-oxa-bicyclo[2.2.1]heptane-2R-carboxylic acid

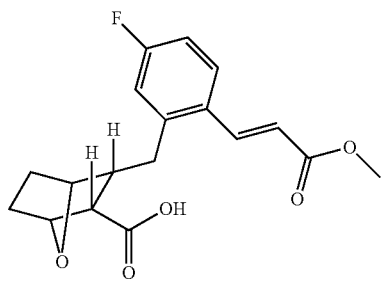 [SMILES: COC(=O)/C=C/c1ccc(F)cc1CC1C2CCC(O2)C1C(=O)O]

To a solution of 3R-(5-Fluoro-2-formyl-benzyl)-7-oxa-bicyclo[2.2.1]heptane-2R-carboxylic acid. (15 g, 54 mmol) in THF (500 mL) at rt and under nitrogen atmosphere, (methoxycarbonylmethylene)triphenylphosphorane (27 g, 81 mmol) was added. The reaction mixture was stirred for 16 hours at rt before concentrating in vacuo. The residue was dissolved in DCM containing 10% of conc. NH$_4$OH:EtOAc (1:9) (150 ml). Triphenylphosphine oxide was removed from the crude product by filtering the ammonium salt through 500 g of silica. The title compound was washed out from silica using 10% AcOH in EtOAc and concentrated in vacuo to yield an off-white solid (13.2 g, 73%).

$^1$H-NMR (CDCl$_3$, 300 MHz) Y 7.91 (d, 1H, =CH), 7.74 (broad s, 1H, —OH), 7.51 (dd, 1H, ArH), 6.92 (m, 2H, ArH), 6.28 (d, 1H, CH=CH), 4.87 (s, 1H, —CH—O), 4.11 (m, 1H, —CH—O—), 3.80 (s, 3H, —OCH$_3$), 2.94-2.73 (m, 1H, —CHCO$_2$, and 1H, —CH—CH$_2$—Ar), 2.65 (m, 1H, —CH—CHH—Ar 1H), 2.28 (m, 1H, —CH—CHH—Ar), 1.57 (m, 2H, —CH$_2$—), 1.40 (m, 1H, —CHH—), 1.25 (m, 1H, —CHH—). $^{19}$F-NMR (CDCl$_3$, 300 MHz) Y −110.4.

LC-MS: m/z 335M+H$^+$

Step 6

3-(2R-{3R-[1-(4-Cyclohexyl-butylcarbamoyl)-2-hydroxy-ethylcarbamoyl]-7-oxa-bicyclo[2.2.1]hept-2-ylmethyl}-4-fluoro-phenyl)-acrylic acid methyl ester

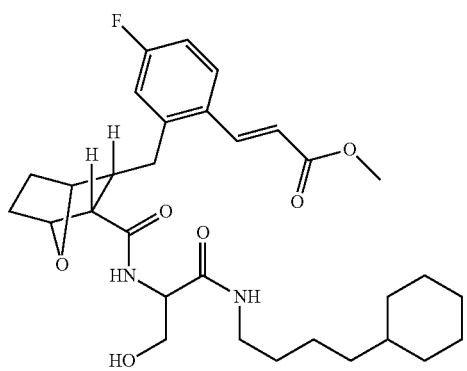 [SMILES: COC(=O)/C=C/c1ccc(F)cc1CC1C2CCC(O2)C1C(=O)NC(CO)C(=O)NCCCCC1CCCCC1]

To a solution of 3R-[5-Fluoro-2-(2-methoxycarbonyl-vinyl)-benzyl]-7-oxa-bicyclo[2.2.1]heptane-2R-carboxylic acid. (13.2 g, 39.5 mmol), 2-amino-N-(4-cyclohexyl-butyl)-3-hydroxy-propionamide (10.5 g, 43.5 mmol and NMM (6.8 ml, 59.3 mmol) in DCM (500 mL) with ice bath cooling, WSC HCl (11.4 g, 59.3 mmol) was added. After 30 minutes the ice bath was removed and the mixture was stirred for 16 hours at rt before concentrating in vacuo. The residue was dissolved in EtOAc washed with HCl (aq. 2M), sat. NaHCO$_3$ and brine. The extract was dried over MgSO$_4$, filtered and the solvent was evaporated under vacuum to give crude product as an off-white solid (12.5 g,).

$^1$H-NMR (CDCl$_3$, 300 MHz) Y 7.87 (d, 1H, =CH), 7.55 (dd, 1H, ArH), 7.46 (d, 1H, —NH), 7.11-6.81 (m, 1H, —NH, 2H, ArH), 6.31 (d, 1H, CH=CH), 4.79 (m, 1H, —CH—O—), 4.50 (m, 1H, —CH—NH), 4.26 (m, 1H, —CH—O—), 4.03 (m, 2H, —CH$_2$OH), 3.81 (s, 3H, —CO$_2$CH$_3$), 3.70 (m, 1H, —OH), 3.12 (m, 2H, —CH$_2$—NH) 0.71-2.90 (m, 25H, —CH—+—CH$_2$—). $^{19}$F-NMR (CDCl$_3$, 300 MHz) Y −110.2.

LC-MS: m/z 559 M+H$^+$

Step 7

(E)-3-(2R-{3R-[4-(4-Cyclohexyl-butylcarbamoyl)-4,5-dihydro-oxazol-2-yl]-7-oxa-bicyclo[2.2.1]hept-2-ylmethyl}-4-fluoro-phenyl)-acrylic acid methyl ester

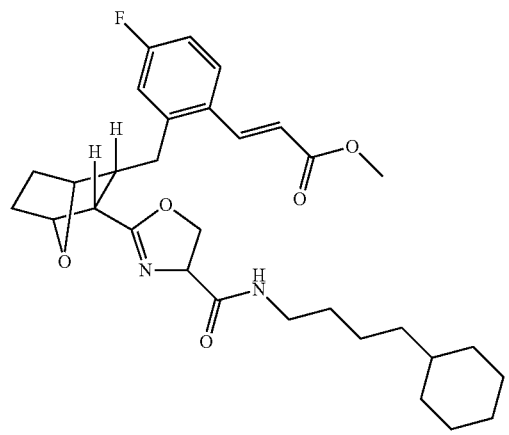 [SMILES: COC(=O)/C=C/c1ccc(F)cc1CC1C2CCC(O2)C1C1=NC(C(=O)NCCCCC2CCCCC2)CO1]

(E)-3R-(2R-{3-[1-(4-Cyclohexyl-butylcarbamoyl)-2-hydroxy-ethylcarbamoyl]-2-hydroxy-ethylcarbamoyl]-7-oxa-bicyclo[2.2.1]hept-2-ylmethyl}-4-fluoro-phenyl)-acrylic acid methyl ester (61) (12.5 g, 22 mmol) was dissolved in dry DCM (1000 mL) at −78° C., under N$_2$. DAST (6.1 mL, 44 mmol) was added and the reaction mixture was stirred for two hours at −78° C. K$_2$CO$_3$ (12.2 g, 88 mmol) was added and the mixture was stirred overnight at room temperature. NaHCO$_3$ saturated solution and DCM were added. The organic phase was separated, washed with brine, dried over MgSO$_4$, filtered and concentrated under vacuum.

The desired product was purified by recrystallisation from diethyl ether to yield an off-white solid (11.0 g, 93% yield).

$^1$H-NMR (CDCl$_3$, 300 MHz) Y 7.89 (d, 1H, J=16 Hz, —CH=CO$_2$Me), 7.60 (m, 1H, ArH), 6.98 (m, 2H, ArH), 6.86 (m, 1H, NH), 6.35 (d, 1H, J=16 Hz, —CH=Ar), 4.86 (m, 1H, —CH—O—), 4.71 (m, 1H, —N—CH—CH$_2$—O), 4.51 (m, 2H, —N—CH—CH$_2$—O), 4.33 (m, 1H, —CH—O—), 3.85 (s, 3H, —CO$_2$CH$_3$), 0.84-3.23 (m, 27H, —CH—+—CH$_2$—). $^{19}$F-NMR (CDCl$_3$, 300 MHz) Y −110.2.

LC-MS: m/z 541M+H$^+$

Step 8

(E)-3-(2R-{3R-[4-(4-Cyclohexyl-butylcarbamoyl)-oxazol-2-yl]-7-oxa-bicyclo[2.2.1]hept-2-ylmethyl}-4-fluoro-phenyl)-acrylic acid methyl ester

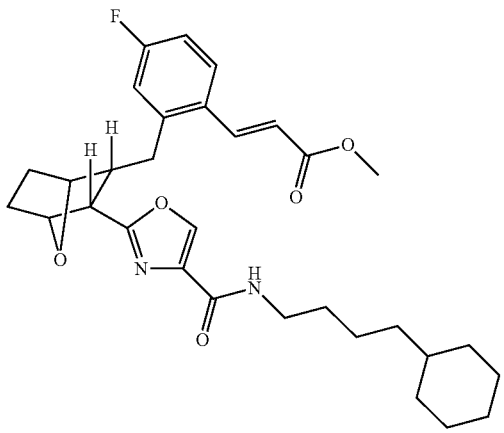 [SMILES: COC(=O)/C=C/c1ccc(F)cc1CC1C2CCC(O2)C1c1nc(C(=O)NCCCCC2CCCCC2)co1]

To a solution of CuBr$_2$ (18.2 g, 81.4 mmol) in dry degassed DCM (350 mL), HMTA (11.4 g, 81.4 mmol) and DBU (12.2 ml, 81.4 mmol) were added at 0° C. and stirred for 10 minutes. (E)-3R-(2R-{3-[4-(4-Cyclohexyl-butylcarbamoyl)-4,5-dihydro-oxazol-2-yl]-7-oxa-bicyclo[2.2.1]hept-2-ylmethyl}-4-fluoro-phenyl)-acrylic acid methyl ester (62) (11 g, 20.3 mmol) in dry degassed DCM (150 mL), was added to the mixture which was stirred overnight at room temperature. The reaction mixture was concentrated in vacuo, suspended in a 1:1 solution of ammonia 33% and saturated solution of NH$_4$Cl (400 ml), extracted with EtOAc, washed with 1M HCl (400 ml) then sat. NaHCO$_3$ (400 ml) and finally brine (400 ml). The organic layer was dried over MgSO$_4$, filtered, and concentrated in vacuo to give a crude product which was purified by recrystallization from diethyl ether. (10.5 g 85% yield). $^1$H-NMR (CDCl$_3$, 300 MHz) Y 8.10 (s, 1H, O—CH═C—N), 7.86 (d, 1H, J=16 Hz, —CH═CO$_2$Me), 7.56 (m, 1H, ArH), 7.14 (m, 1H, ArH), 6.91 (m, 1H, ArH), 6.32 (d, 1H, J=16 Hz, —CH═Ar), 5.00 (m, 1H, —CH—O—), 4.37 (m, 1H, —CH—O—), 3.85 (s, 3H, —CO$_2$CH$_3$), 3.41 (m, 3H, NH—CH+N═C—CH), 3.07 (m, 1H, CH—CH$_2$—Ar), 2.43 (m, 2H, CH$_2$—Ar), 0.85-1.85 (m, 21H, —CH—+—CH$_2$—). $^{19}$F-NMR (CDCl$_3$, 300 MHz) Y −110.6.

LC-MS: m/z 539 M+H$^+$

Step 9

((E)-3-(2R-{3R-[4-(4-Cyclohexyl-butylcarbamoyl)-oxazol-2-yl]-7-oxa-bicyclo[2.2.1]hept-2-ylmethyl}-4-fluoro-phenyl)-acrylic acid

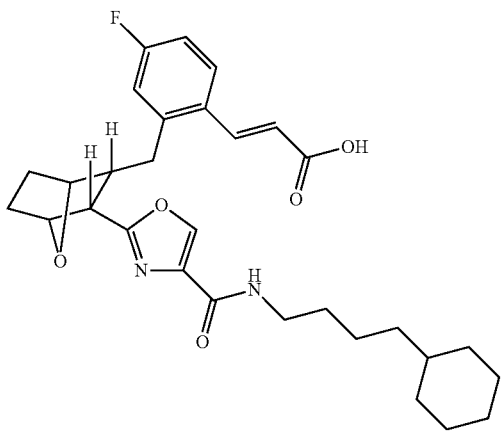 [SMILES: O=C(O)/C=C/c1ccc(F)cc1CC1C2CCC(O2)C1c1nc(C(=O)NCCCCC2CCCCC2)co1]

(E)-3R-(2R-{3-[4-(4-Cyclohexyl-butylcarbamoyl)-oxazol-2-yl]-7-oxa-bicyclo[2.2.1]hept-2-ylmethyl}-4-fluoro-phenyl)-acrylic acid methyl ester (5.5 g, 10.2 mmol) was dissolved in THF (30 mL), MeOH (165 ml) and 1M NaOH (65 ml, 65 mmol) was added. The mixture stirred 5 hours at room temperature, acidified with 1M HCl (100 ml, 100 mmol) extracted with DCM (2×200 ml) dried over MgSO$_4$, filtered and concentrated in vacuo. The crude product was recrystallized from diethyl ether to yield the titled compound as a white solid. (4.9 g, 92% yield). $^1$H-NMR (CDCl$_3$, 300 MHz) Y 8.19 (s, 1H, 0-CH═C—N), 7.92 (d, 1H, J=16 Hz, —CH═CO$_2$Me), 7.58 (m, 1H, ArH), 7.14 (m, 1H, ArH), 6.93 (m, 1H, ArH), 6.33 (d, 1H, J=16 Hz, —CH═Ar), 5.01 (m, 1H, —CH—O—), 4.39 (m, 1H, —CH—O—), 3.41 (m, 4H, NH—CH$_2$+N═C—CH+CH—CH$_2$—Ar), 0.83-2.57 (m, 24H, —CH—+—CH$_2$—). $^{19}$F-NMR (CDCl$_3$, 300 MHz) Y −110.0.

LC-MS: m/z 525M+H$^+$

EXAMPLES 2 AND 3

The preparation of the compounds of this invention, as disclosed above, wherein the cyclobutyl group is replaced by an octyl or nonyl group are made by substitution of the appropriate reactant. The structures of the compounds of the nonyl and octyl derivatives are given in the SAR Table, as Examples 2 and 3, below.

The saturated compounds of Examples 4 through 6 are prepared as follows:

EXAMPLE 4

3-{2R-[3R-(4-Nonylcarbamoyl-oxazol-2-yl)-7-oxa-bicyclo[2.2.1]hept-2-ylmethyl]-4-fluoro-phenyl}-propionic acid

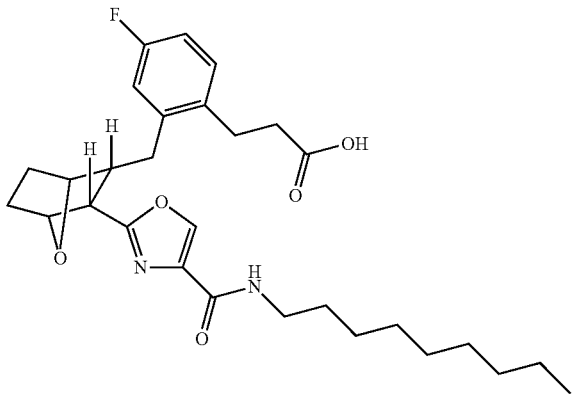 [SMILES: CCCCCCCCCNC(=O)c1coc(C2C3CCC(O3)C2Cc2cc(F)ccc2CCC(=O)O)n1]

Step 1

(E)-3-[4-Fluoro-2-((S)-5-oxo-4,10-dioxa-tricyclo[5.2.1.0*2,6*]dec-3-yl)-phenyl]-acrylic acid methyl ester

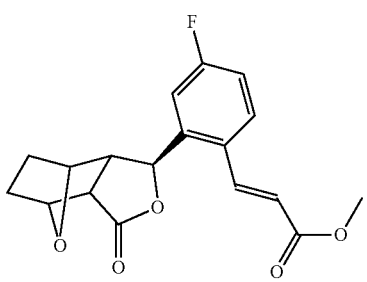 [SMILES: COC(=O)/C=C/c1ccc(F)cc1[C@H]1OC(=O)C2C3CCC(O3)C21]

To a solution of 4-Fluoro-2-(5-oxo-4,10-dioxa-tricyclo[5, 2R,1R,0*2,6*]dec-3S-yl)-benzaldehyde (Example 1, step 2) (5 g, 18.1 mmol) and lithium chloride (0.921 g, 21.72 mmol) in acetonitrile (30 ml) under nitrogen atmosphere, trimethylphosphonoacetate (3.13 mL, 21.72 mmol) was added followed by DBU (6.5 mL, 43.44 mmol). The resulting mixture was stirred at room temperature for 2 h. After this time it was poured over saturated solution of NaHCO$_3$ (100 mL) and extracted with dichloromethane (2×100 mL). The combined organic layers were dried over MgSO$_4$, filtered and concentrated in vacuo yielding the titled compound as thick oil.

Step 2

3-[5-Fluoro-2-(2-methoxycarbonyl-ethyl)-benzyl]-7-oxa-bicyclo[2.2.1]heptane-2-carboxylic acid

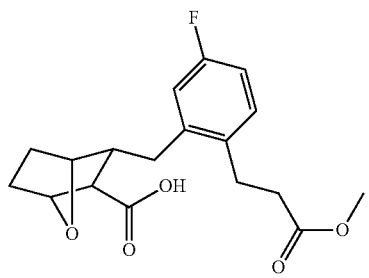 [SMILES: COC(=O)CCc1ccc(F)cc1CC1C2CCC(O2)C1C(=O)O]

To a solution of (E)-3-[4-Fluoro-2-((S)-5-oxo-4,10-dioxa-tricyclo[5.2.1.0*2,6]dec-3-yl)-phenyl]-acrylic acid methyl ester (18.1 mmol) in a mixture 2:1 methanol/tetrahydrofuran (75 ml), palladium hydroxide (0.61 g) was added. The flask was evacuated and then connected to a balloon filled with hydrogen. The reaction was stirred at room temperature for 2 h, and a second portion of palladium hydroxide (0.61 g) was added. The flask was evacuated and then connected to a balloon filled with hydrogen. After another 2 h, the balloon was removed and Celite (1 g) was added to the mixture, which was stirred for 10 minutes. The mixture was filtered through a Celite pad and the pad was washed with methanol (25 mL). The filtrate was evaporated to provide yellow oil. The oil was dissolved in dichloromethane (50 mL) and dried over MgSO$_4$.

Then, the solution was filtered and concentrated in vacuo and the residue was dissolved in ethyl acetate (60 mL) and treated with Darco KB activated carbon by heating at reflux for 2 minutes and then cooling. Celite (1.2 g) was added and the mixture stirred for 10 minutes and then filtered through a pad of Celite. The pad was washed with ethyl acetate (25 mL). The filtrate was evaporated and the residue was crystallized from hot ethyl acetate (11.5 mL) and heptane (23 mL). After cooling to room temperature, additional heptane (30 mL) was added and the mixture was left to stand at 4° C. overnight.

Then, I filtered the solid and washed with more heptane and dried under vacuo overnight yielding the titled compound as a colourless solid. (5.36 g, 88%)

$^1$H-NMR (CDCl$_3$, 300 MHz) γ 7.11 (dd, 1H, J=5.7, 8.6 Hz, ArH), 6.88 (m, 2H, ArH), 4.88 (m, 1H, —CH—O—), 4.27 (m, 1H, —CH—O), 3.66 (s, 3H, CO$_2$CH$_3$), 2.92 (m, 3H, —CH$_2$—CH$_2$—CO$_2$Me and —CH—CO$_2$H), 2.72 (m, 1H, —CH—), 2.50 (m, 4H, —CH$_2$—CH$_2$—CO$_2$Me and —CH$_2$—Ar), 1.74 (m, 2H, —CH$_2$—CH$_2$—), 1.54-1.25 (m, 2H, —CH$_2$—CH$_2$—).

Step 3

3-{4-Fluoro-2-[3-(2-hydroxy-1-nonylcarbamoyl-ethylcarbamoyl)-7-oxa-bicyclo[2.2.1]hept-2-ylmethyl]-phenyl}-propionic acid methyl ester

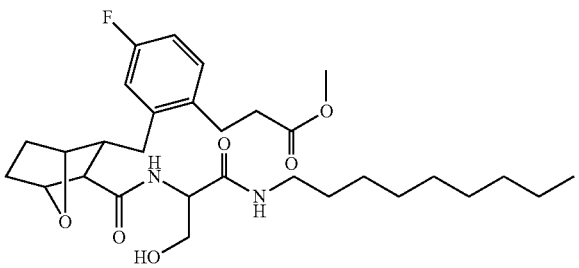 [SMILES: CCCCCCCCCNC(=O)C(CO)NC(=O)C1C2CCC(O2)C1Cc1cc(F)ccc1CCC(=O)OC]

To a solution of 3-[5-Fluoro-2-(2-methoxycarbonyl-ethyl)-benzyl]-7-oxa-bicyclo[2.2.1]heptane-2-carboxylic acid (5 g, 14.86 mmol) and nonylserinamide (3.77 g, 16.35 mmol) in dimethylformamide (150 ml) under nitrogen atmosphere, N-methylmorpholine (3.6 mL, 32.7 mmol) was added followed by HBTU (6.2 g, 16.35 mmol). The resulting mixture was stirred at room temperature for 16 h.

After this time the solution was concentrated under vacuum and the residue was dissolved in ethyl acetate (100 mL). Then, it was washed with a 2M HCl solution (100 mL), saturated solution of NaHCO$_3$ (100 mL) and dried over MgSO$_4$. Filtration and concentrated in vacuum yield the titled compound as thick oil.

LC-MS (M+1): 549

Step 4

3-{4-Fluoro-2-[3-(4-nonylcarbamoyl-4,5-dihydro-oxazol-2-yl)-7-oxa-bicyclo[2.2.1]hept-2-ylmethyl]-phenyl}-propionic acid methyl ester

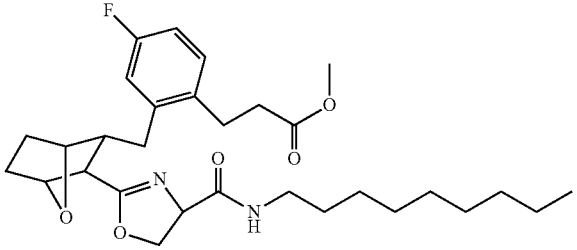 [SMILES: CCCCCCCCCNC(=O)C1COC(C2C3CCC(O3)C2Cc2cc(F)ccc2CCC(=O)OC)=N1]

To a solution of 3-{4-Fluoro-2-[3-(2-hydroxy-1-nonylcarbamoyl-ethylcarbamoyl)-7-oxa-bicyclo[2.2.1]hept-2-ylmethyl]-phenyl}-propionic acid methyl ester (14.86 mmol) in dichloromethane (200 ml), at −78° C. and under nitrogen atmosphere, DAST (3.93 mL, 29.72 mmol) was added and the resulting mixture was stirred at room temperature for 2.5 h. After this time, potassium carbonate (4.11 g, 29.72 mmol) was added and the solution was stirred for another hour. Then saturated solution of NaHCO$_3$ (200 mL) was added and the mixture was extracted with ethyl acetate (200 mL). Then, it was washed with Brine (150 mL), and dried over MgSO$_4$. Filtration and concentrated in vacuo yield the crude compound as thick oil.

The residue was purified by column chromatography in silica using a solvent gradient starting from Ethyl acetate/iso-hexane 1:1 to Ethyl acetate/methanol 9:1 to isolate the titled compound as thick oil (4.7 g, 60%)

$^1$H-NMR (CDCl$_3$, 300 MHz) γ 7.11 (dd, 1H, J=5.7, 8.6 Hz, ArH), 6.87 (m, 2H, ArH), 6.63 (m, 1H, NH), 4.87 (m, 1H, —CH—O—), 4.59 (m, 1H, =N—CH—CON—), 4.40 (m, 2H, O—CH$_2$—), 4.31 (m, 1H, —CH—O), 3.67 (s, 3H, CO$_2$CH$_3$), 3.23 (m, 2H, —CONH—CH$_2$—), 2.94 (m, 3H, —CH$_2$—CH$_2$—CO$_2$Me and —CH—), 2.65-2.40 (m, 5H, —CH$_2$—CH$_2$—CO$_2$Me, —CH— and —CH$_2$—Ar), 1.76 (m, 2H, —CH$_2$—CH$_2$—), 1.55-1.44 (m, 4H, —CH$_2$—CH$_2$— and —CO—NH—CH$_2$—CH$_2$—), 1.27 (m, 12H, —CH$_2$—CH$_2$—), 0.88 (m, 3H, —CH$_3$).

LC-MS (M+1): 531

Step 5

3-{4-Fluoro-2-[3-(4-nonylcarbamoyl-oxazol-2-yl)-7-oxa-bicyclo[2.2.1]hept-2-ylmethyl]-phenyl}-propionic acid methyl ester

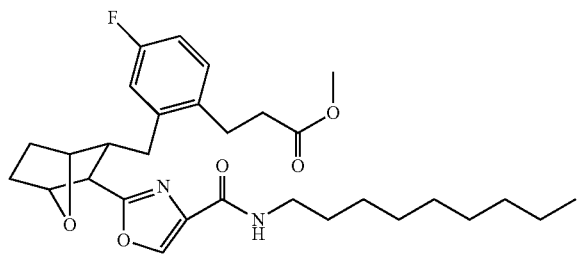 [SMILES: CCCCCCCCCNC(=O)c1coc(C2C3CCC(O3)C2Cc2cc(F)ccc2CCC(=O)OC)n1]

To a suspension of Copper bromide (6.27 g, 28.08 mmol) in dichloromethane (90 mL), under nitrogen atmosphere and in a water bath, was added HMTA (3.94 g, 28.08 mmol) followed by DBU (4.17 mL, 28.08 mmol) and the resulting mixture was stirred for 15 minutes. Then, a solution of (3-{4-Fluoro-2-[3-(4-nonylcarbamoyl-4,5-dihydro-oxazol-2-yl)-7-oxa-bicyclo[2.2.1]hept-2-ylmethyl]-phenyl}-propionic acid methyl ester (3.72 g, 7.02 mmol) in dichloromethane (40 ml) was added and the resulting mixture was stirred at room temperature for 16 h.

After this time, the solution was concentrated under vacuum and the residue was partitioned between ethyl acetate (100 mL) and 1:1 sat. solution of NH$_4$Cl and NH$_3$ (100 mL). Then, the organic layer was separated and washed with Brine (100 mL), and dried over MgSO$_4$. Filtration and concentrated in vacuo yield the crude compound as thick oil.

The residue was purified by column chromatography in silica using Ethyl acetate/iso-hexane 5:1 to isolate the titled compound as a yellow solid (2.2 g, 60%)

$^1$H-NMR (CDCl$_3$, 300 MHz) γ 8.07 (s, 1H, =CH), 7.08 (dd, 1H, J=5.7, 8.6 Hz, ArH), 7.00 (m, 1H, NH), 6.83 (m, 2H, ArH), 4.99 (m, 1H, —CH—O—), 4.37 (m, 1H, —CH—O), 3.66 (s, 3H, CO$_2$CH$_3$), 3.39 (m, 3H, —CH— and —CONH—CH$_2$—), 2.83 (m, 2H, —CH$_2$—CO$_2$Me), 2.63-2.48 (m, 3H, —CH$_2$—CH$_2$—CO$_2$Me and —CH—), 2.35 (m, 1H, —CH$_2$Ar), 2.21 (m, 1H, —CH$_2$Ar), 1.83 (m, 2H, —CH$_2$—CH$_2$—), 1.63-1.25 (m, 4H, —CH$_2$—CH$_2$— and —CO—NH—CH$_2$—CH$_2$—), 1.25 (m, 12H, —CH$_2$—CH$_2$—), 0.91 (m, 3H, —CH$_3$).

$^{19}$F-NMR (CDCl$_3$, 300 MHz) γ −117

Step 6

3-{2R-[3R-(4-Nonylcarbamoyl-oxazol-2-yl)-7-oxa-bicyclo[2.2.1]hept-2-ylmethyl]-4-fluoro-phenyl}-propionic acid

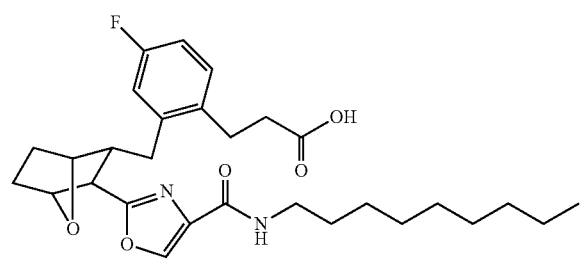 [SMILES: CCCCCCCCCNC(=O)c1coc(C2C3CCC(O3)C2Cc2cc(F)ccc2CCC(=O)O)n1]

To a solution of 3-{4-Fluoro-2-[3-(4-nonylcarbamoyl-oxazol-2-yl)-7-oxa-bicyclo[2.2.1]hept-2-ylmethyl]-phenyl}-propionic acid methyl ester 7 (1.39 g, 2.63 mmol) in tetrahydrofuran (40 ml) was added a solution of Lithium hydroxide (0.441 g, 10.52 mmol) in water (10 mL) and the resulting mixture was stirred at room temperature for 16 h. After this time, the solution was partitioned between ethyl acetate (100 mL) and 2M HCl solution (50 mL). Then, the organic layer was separated and washed with Brine (50 mL), and dried over MgSO$_4$. Filtration and concentrated in vacuo yield the titled compound as slight yellow solid. (1.24 g, 92%)

$^1$H-NMR (CDCl$_3$, 300 MHz) γ 8.15 (s, 1H, =CH), 7.17 (m, 1H, NH), 7.10 (dd, 1H, J=5.7, 8.6 Hz, ArH), 6.84 (m, 2H, ArH), 4.99 (m, 1H, —CH—O—), 4.39 (m, 1H, —CH—O), 3.41 (m, 3H, —CH— and —CONH—CH$_2$—), 2.85 (m, 2H, —CH$_2$—CO$_2$Me), 2.62-2.50 (m, 3H, —CH$_2$—CH$_2$—CO$_2$Me and —CH—), 2.36 (m, 1H, —CH$_2$Ar), 2.20 (m, 1H, —CH$_2$Ar), 1.84 (m, 2H, —CH$_2$—CH$_2$—), 1.63-1.25 (m, 4H, —CH$_2$—CH$_2$— and —CO—NH—CH$_2$—CH$_2$—), 1.27 (m, 12H, —CH$_2$—CH$_2$—), 0.88 (m, 3H, —CH$_3$).

EXAMPLES 5 AND 6

The preparation of the compounds of this invention, as disclosed above, wherein the nonyl group is replaced by an octyl or cyclohexyl-n-butyl group are made by substitution of the appropriate reactant. The structures of the octyl and cyclohexyl-n-butyl derivatives, i.e. Examples 5 and 6, are given in the SAR Table, below.

Figure 13:
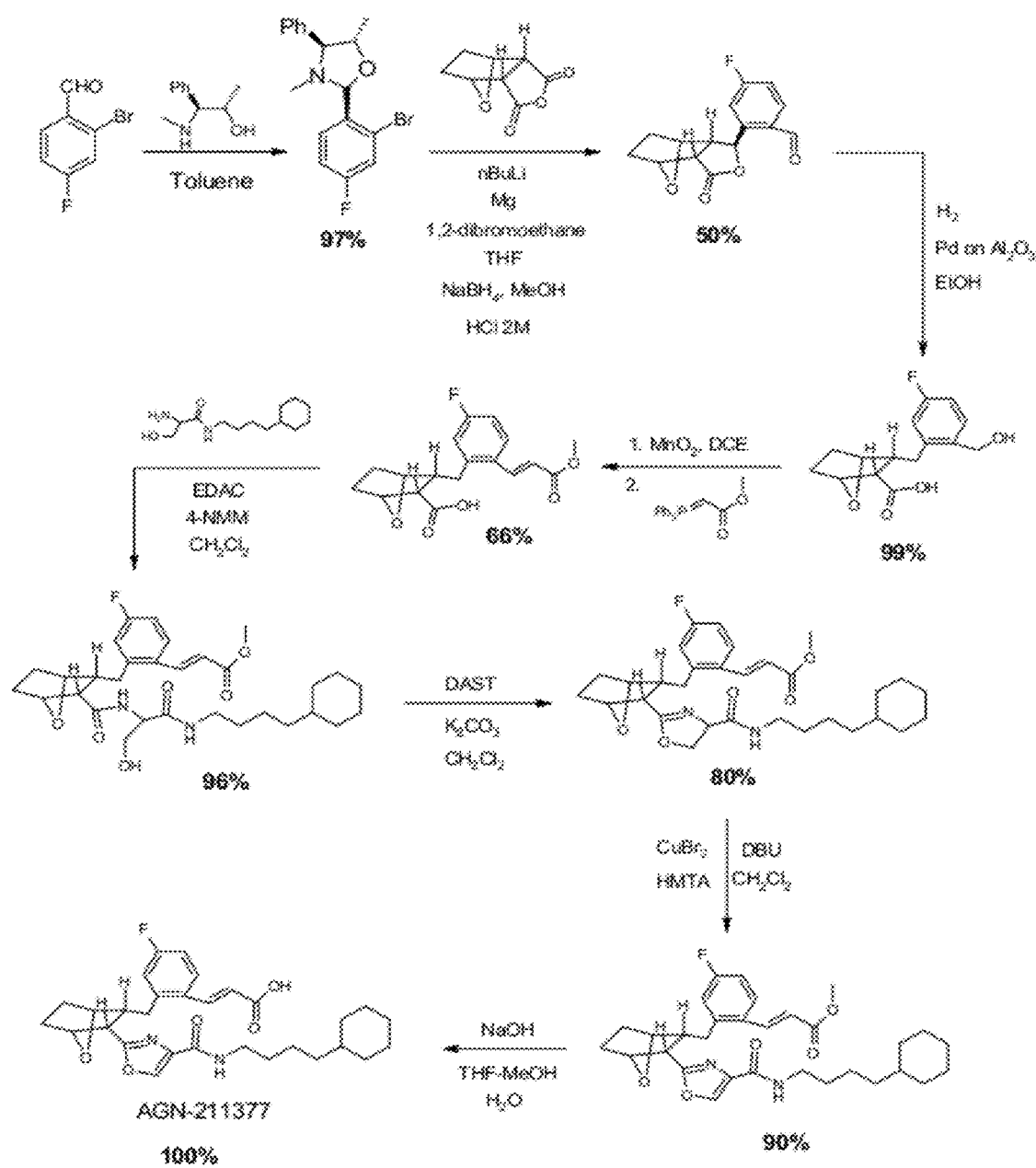
FIG. 13 shows a synthetic scheme for the production of the compounds of the present invention.

In view of the above Examples and as shown in FIG. 13, the present invention provides a method for the preparation of (E)-3-(2R-{3R-[4-(4-Alkylcarbamoyl)-oxazol-2-yl]-7-oxa-bicyclo[2.2.1]hept-2-ylmethyl}-4-fluoro-phenyl)-acrylic acid and propionic acid and lower alkyl esters thereof, e.g. (E)-3-(2R-{3R-[4-(4-Cyclohexyl-butylcarbamoyl)-oxazol-2-yl]-7-oxa-bicyclo[2.2.1]hept-2-ylmethyl}-4-fluoro-phenyl)-acrylic acid,

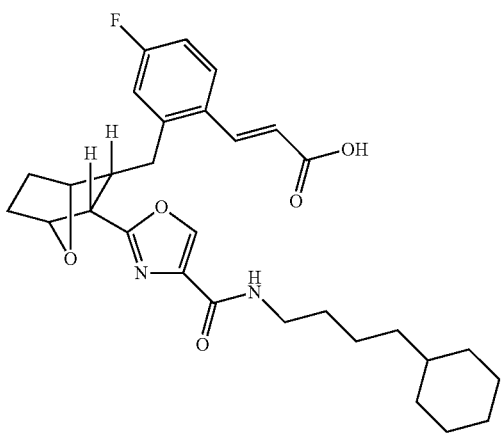 [SMILES: O=C(O)/C=C/c1ccc(F)cc1CC1C2CCC(O2)C1c1nc(C(=O)NCCCCC2CCCCC2)co1]

Which, for example, comprises hydrolyzing (E)-3R-(2R-{3-[4-(4-Cyclohexyl-butylcarbamoyl)-oxazol-2-yl]-7-oxa-bicyclo[2.2.1]hept-2-ylmethyl}-4-fluoro-phenyl)-acrylic acid alkyl ester.

Preferably, this method comprises hydrolyzing a solution of (E)-3R(2R{3-[4-(4-Cyclohexyl-butylcarbamoyl)-oxazol-2-yl]-7-oxa-bicyclo[2.2.1]hept-2-ylmethyl}-4-fluoro-phenyl)-acrylic acid methyl ester in THF and MeOH in the presence of NaOH, at room temperature, acidifying the resulting solution with HCl, extracting the acidified solution with DCM, drying the extract over MgSO₄, filtering and concentrating the dried extract in vacuo and recrystallizing said vacuum concentrated extract from diethyl ether to yield E)-3-(2R-{3R-[4-(4-Cyclohexyl-butylcarbamoyl)-oxazol-2-yl]-7-oxabicyclo[2.2.1]hept-2-ylmethyl}-4-fluoro-phenyl)-acrylic acid as a white solid.

In this method (E)-3-(2R-{3R-[4-(4-Cyclohexyl-butylcarbamoyl)-oxazol-2-yl]-7-oxa-bicyclo[2.2.1]hept-2-ylmethyl}-4-fluoro-phenyl)-acrylic acid methyl ester

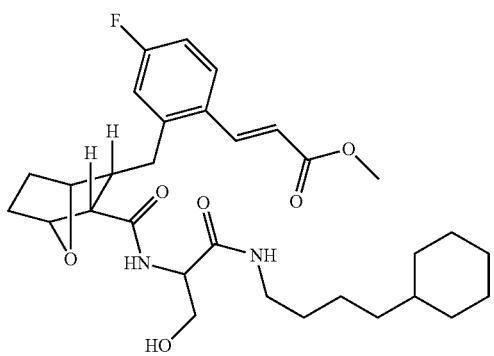 [SMILES: COC(=O)/C=C/c1ccc(F)cc1CC1C2CCC(O2)C1C(=O)NC(CO)C(=O)NCCCCC1CCCCC1]

is prepared by reacting a solution of 3R-[5-Fluoro-2-(2-methoxycarbonyl-vinyl)-benzyl]-7-oxa-bicyclo[2.2.1]heptane-2R-carboxylic acid with 2-amino-N-(4-cyclohexyl-butyl)-3-hydroxy-propionamide and NMM and said reaction may take place in DCM at 0° C.

The (E)-3-(2R-{3R-[4-(4-Cyclohexyl-butylcarbamoyl)-oxazol-2-yl]-7-oxa-bicyclo[2.2.1]hept-2-ylmethyl}-4-fluoro-phenyl)-acrylic acid methyl ester solution in DCM may be treated with HCl, concentrated under vacuum, dissolved in EtOAc, washed with HCl, saturated NaHCO₃ and brine, dried over MgSO₄, filtered and evaporated under vacuum to yield a crude (E)-3-(2R-{3R-[4-(4-Cyclohexyl-butylcarbamoyl)-oxazol-2-yl]-7-oxa-bicyclo[2.2.1]hept-2-ylmethyl}-4-fluoro-phenyl)-acrylic acid methyl ester as an off-white solid.

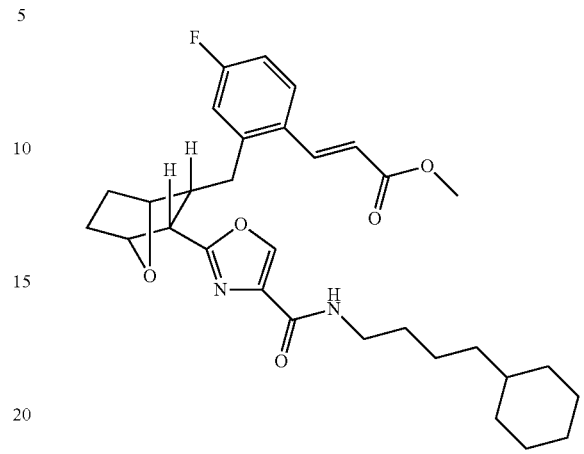

In view of the above Examples and as shown in FIG. 13, the present invention provides a method for the preparation of (E)-3-(2R-{3R-[4-(4-Alkylcarbamoyl)-oxazol-2-yl]-7-oxa-bicyclo[2.2.1]hept-2-ylmethyl}-4-fluoro-phenyl)-acrylic acid and propionic acid and lower alkyl esters thereof, e.g. (E)-3-(2R-{3R-[4-(4-Cyclohexyl-butylcarbamoyl)-oxazol-2-yl]-7-oxa-bicyclo[2.2.1]hept-2-ylmethyl}-4-fluoro-phenyl)-acrylic acid,

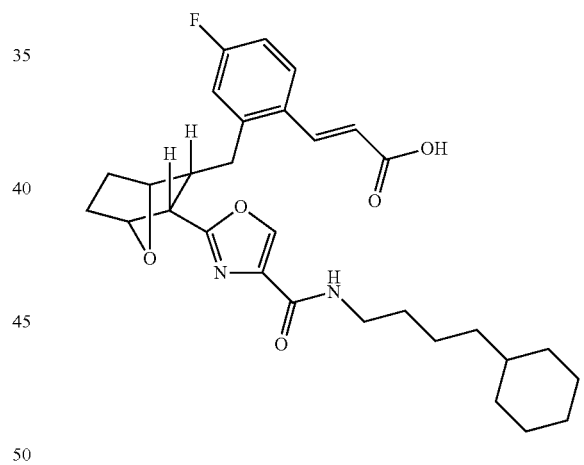

Which, for example, comprises hydrolyzing (E)-3R-(2R-{3-[4-(4-Cyclohexyl-butylcarbamoyl)-oxazol-2-yl]-7-oxa-bicyclo[2.2.1]hept-2-ylmethyl}-4-fluoro-phenyl)-acrylic acid alkyl ester.

Preferably, this method comprises hydrolyzing a solution of (E)-3R(2R{3-[4-(4-Cyclohexyl-butylcarbamoyl)-oxazol-2-yl]-7-oxa-bicyclo[2.2.1]hept-2-ylmethyl}-4-fluoro-phenyl)-acrylic acid methyl ester in THF and MeOH in the presence of NaOH, at room temperature, acidifying the resulting solution with HCl, extracting the acidified solution with DCM, drying the extract over MgSO₄, filtering and concentrating the dried extract in vacuo and recrystallizing said vacuum concentrated extract from diethyl ether to yield E)-3-(2R-{3R-[4-(4-Cyclohexyl-butylcarb amoyl)-oxazol-2-yl]-7-oxabicyclo[2.2.1]hept-2-ylmethyl}-4-fluoro-phenyl)-acrylic acid as a white solid.

In this method (E)-3-(2R-{3R-[4-(4-Cyclohexyl-butylcarbamoyl)-oxazol-2-yl]-7-oxa-bicyclo[2.2.1]hept-2-ylmethyl}-4-fluoro-phenyl)-acrylic acid methyl ester

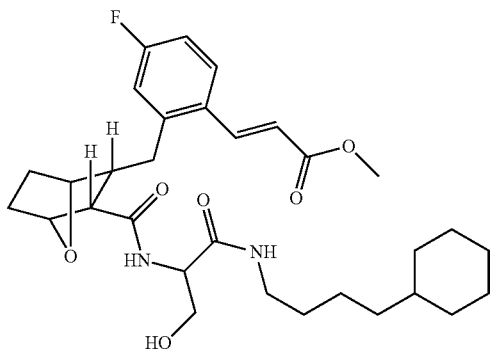 [SMILES: COC(=O)/C=C/c1ccc(F)cc1CC1C2CCC(O2)C1C(=O)NC(CO)C(=O)NCCCCC1CCCCC1]

is prepared by reacting a solution of 3R-[5-Fluoro-2-(2-methoxycarbonyl-vinyl)-benzyl]-7-oxa-bicyclo[2.2.1]heptane-2R-carboxylic acid with 2-amino-N-(4-cyclohexyl-butyl)-3-hydroxy-propionamide and NMM and said reaction may take place in DCM at 0° C.

The (E)-3-(2R-{3R-[4-(4-Cyclohexyl-butylcarbamoyl)-oxazol-2-yl]-7-oxa-bicyclo[2.2.1]hept-2-ylmethyl}-4-fluoro-phenyl)-acrylic acid methyl ester solution in DCM may be treated with HCl, concentrated under vacuum, dissolved in EtOAc, washed with HCl, saturated NaHCO$_3$ and brine, dried over MgSO$_4$, filtered and evaporated under vacuum to yield a crude (E)-3-(2R-{3R-[4-(4-Cyclohexyl-butylcarbamoyl)-oxazol-2-yl]-7-oxa-bicyclo[2.2.1]hept-2-ylmethyl}-4-fluoro-phenyl)-acrylic acid methyl ester as an off-white solid.

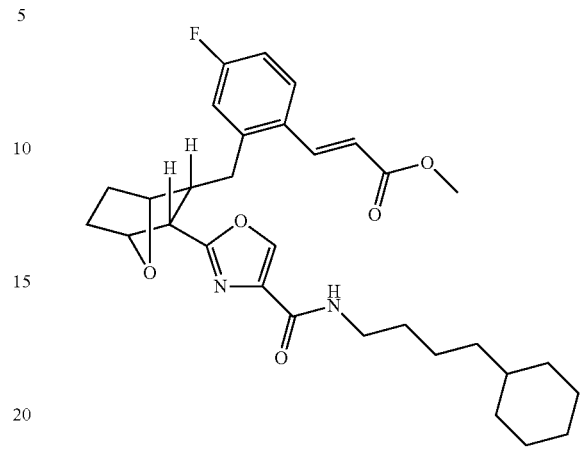

The above compounds were tested for PG antagonist activity as follows using human recombinant prostanoid receptor (DP$_1$, EP$_{1-4}$, FP, IP and TP) stable cell lines:

In order to measure the response of G$_s$ and G$_i$ coupled prostanoid receptors as a Ca$^{2+}$ signal, chimeric G protein cDNAs were used. Stable cell lines over-expressing human prostanoid DP$_1$, EP$_{1-4}$, FP, IP, and TP receptors were established as described in U.S. Ser. No. 61/410,153.

| STRUCTURE | | FP | DP | EP1 | EP2 | EP3 | EP4 | IP | TP |
|---|---|---|---|---|---|---|---|---|---|
| Example 1 | (structure) | 59 | 71 | 380 | NA | 5500 | 60 | NA | <1 |
| Example 2 | (structure) | 300 | 220 | 2000 | NA | NA | 120 | NA | <1 |

-continued

| STRUCTURE | FP | DP | EP1 | EP2 | EP3 | EP4 | IP | TP |
|---|---|---|---|---|---|---|---|---|
| Example 3 (structure) | 230 | 270 | 4100 | NA | NA | 180 | NA | <1 |
| Example 4 (structure) | 12 | 17 | 660 | 4300 | 4100 | 92 | 1900 | <1 |
| Example 5 (structure) | 25 | 55 | 1400 | NA | 4700 | 160 | 2400 | <1 |
| Example 6 (structure) | 35 | 50 | 1750 | NA | NA | 170 | NA | <1 |

As shown in the TABLE, the compounds of the Examples are selective for the DP, EP1, EP4, FP and TP receptors and not the EP2 or IP receptors and thus have the desired biological profile described above.

The compound of Example 1 was also evaluated for activity in an in-vivo Rat Experimental Autoimmune Uveoretinitis (EAU) model and a model of retinal neovascularization.

EXAMPLE 7

Experimental autoimmune uveoretinitis (EAU) is a T helper type 1 cell-mediated autoimmune disease, which serves as a model of human chronic uveitis. In this model, cells of monocyte/macrophage lineage and retinal antigen (Ag)-specific T cells infiltrate into the retina and cause inflammatory lesion, where pro-inflammatory cytokines and various stimuli activate a transcriptional factor, nuclear factor-$_\kappa$B (NF-$_\kappa$B), which modulates inflammation and enhances immune responses.

Rodent models of EAU induced by major uveitis autoantigens, S-antigen (S-Ag) or A-Antigen-M18 peptide and interphotoreceptor retinoid binding protein (IRBP) or R16 peptide are used to identify the efficacy of various molecule and biologic therapeutics and evaluate the safety of anti-inflammatory therapies.

It has been found that immunization with 50 μg of soluble retinal protein peptide (M18) or 30 μg of photoreceptor proteins peptide (R16) formulated with Freund's complete adjuvant *mycobacterium tuberculosis* H3Ra by footpad injection in rat causes robust and reproducible development of EAU. The ocular inflammatory response in the EAU eyes will initiate in one-week post administration, reach its peak at 14-16 days and then subside at three to four weeks. This model was used for testing the compound of EXAMPLE 1 for anti-inflammatory efficacy.

Prostaglandins (PGE, PGF, and PGD) have a variety of physiological effects including the activation of the inflammatory response. When tissues are damaged, white blood cells flood to the site; Prostaglandins are produced via the cyclooxygenase pathway (COX) and activated by binding to their membrane receptors to regulate tissue cell responses. It has been shown that 1) the expression of $EP_2$, $EP_4$, and FP receptors is excited in human ciliary epithelial and ciliary muscle cells, 2) inhibition of prostaglandin receptor reduces ocular inflammatory reaction; and 3) the prostaglandin receptor antagonists reduce the PGs mediated ocular diseases or conditions, such as acute and chronic uveitis.

The anti-inflammatory effect of PG antagonist of EXAMPLE 1 (as compared to vehicle, alone, the compound of EXAMPLE 8, which blocks DP1, EP4, FP and TP receptors; SC-51322, which blocks the EP1 receptor, only, and the combination of EXAMPLE 8 and SC-51322) was measured. In this test, EAU is induced by administering M18 peptide of S-Ag by ip injection from day −1 to 13 to rats. This test demonstrates that if the multiple prostaglandin receptors involved in the chronic ocular inflammatory diseases are blocked inflammatory symptoms are not manifested. (See http://www.iuphardb.org/DATABASE/LigandDisplayForward?ligandId=1924 for the description of SC-51322.)

As shown in FIG. 14 (Anti-inflammation-Summary) the compound of EXAMPLE 1 obtains a better clinical score than any of the comparators except the combination of 3-(2-{(1S,2R,3S)-3-[4-(4-Cyclohexyl-butylcarbamoyl)-oxazol-2-yl]-7-oxa-bicyclo[2.2.1]hept-2-ylmethyl}-4-fluoro-phenyl)-propionic acid and SC-51322 and a lower amount of protein and invasive cells in the aqueous humor than all of the comparators. In addition, since it has been found that the combination of 3-(2-{(1S,2R,3S)-3-[4-(4-Cyclohexyl-butylcarbamoyl)-oxazol-2-yl]-7-oxa-bicyclo[2.2.1]hept-2-ylmethyl}-4-fluoro-phenyl)-propionic acid and SC-51322 inhibits ocular inflammation, it is clear that the compound of EXAMPLE 1, which has the same biological profile as the combination, would also be effective for treating ocular inflammation. Furthermore, as representative of the other compounds utilized in the pharmaceutical compositions and methods of treatment of this invention, said other compounds will also be useful for treating and/or preventing ocular and other inflammatory conditions.

EXAMPLE 8

3-(2-{(1S,2R,3S)-3-[4-(4-Cyclohexyl-butylcarbamoyl)-oxazol-2-yl]-7-oxa-bicyclo[2.2.1]hept-2-ylmethyl}-4-fluoro-phenyl)-propionic acid is a PG antagonist which is selective for DP1, EP4, FP and TP receptors.

EXAMPLE 9

The compound of Example 1 was also evaluated for activity in an in-vivo Rat laser-induced neovascularization (CNV) model.

(CNV) Chronic inflammation is a critical component of neovascularization progression.

Prostaglandin $E_2$ ($PGE_2$), once viewed as the prototypical mediator of inflammation, is now regarded as a promoter of neoplastic growth and of neovascularization. Several studies have delineated the molecular mechanisms utilized by $PGE_2$ to induce proliferation. $PGE_2$ upon binding to its membrane receptor, belonging to the classical G protein-coupled receptor family, activates a signal cascade that through a complex array of intermediate steps (c-Src, PKC, Pyk2), leads to the extracellular release of peptide ligands stimulating growth factor receptors and producing tumor growth. In parallel, $PGE_2$ transactivates the EGF receptor (EGFR) via an intracellular phosphorylation cascade involving the protooncogene c-Src, which magnifies the EGF angiogenesis drive.

The angiostatic effect of the PG antagonist of EXAMPLE 1 (as compared to vehicle, alone, the compound of EXAMPLE 8, which blocks DP1, EP4, FP and TP receptors; SC-51322, which blocks the EP1 receptor, only, and the combination of EXAMPLE 8 and SC-51322) was measured. In this test, compounds were formulated in 70% polyethylene glycol (PEG). CNV is induced by laser burn. This test demonstrates that if the multiple prostaglandin receptors involved in the chronic ocular inflammatory diseases are blocked, neovascularization, just like the inflammatory responses in the above EAU model, is also not manifested.

Figure 15:
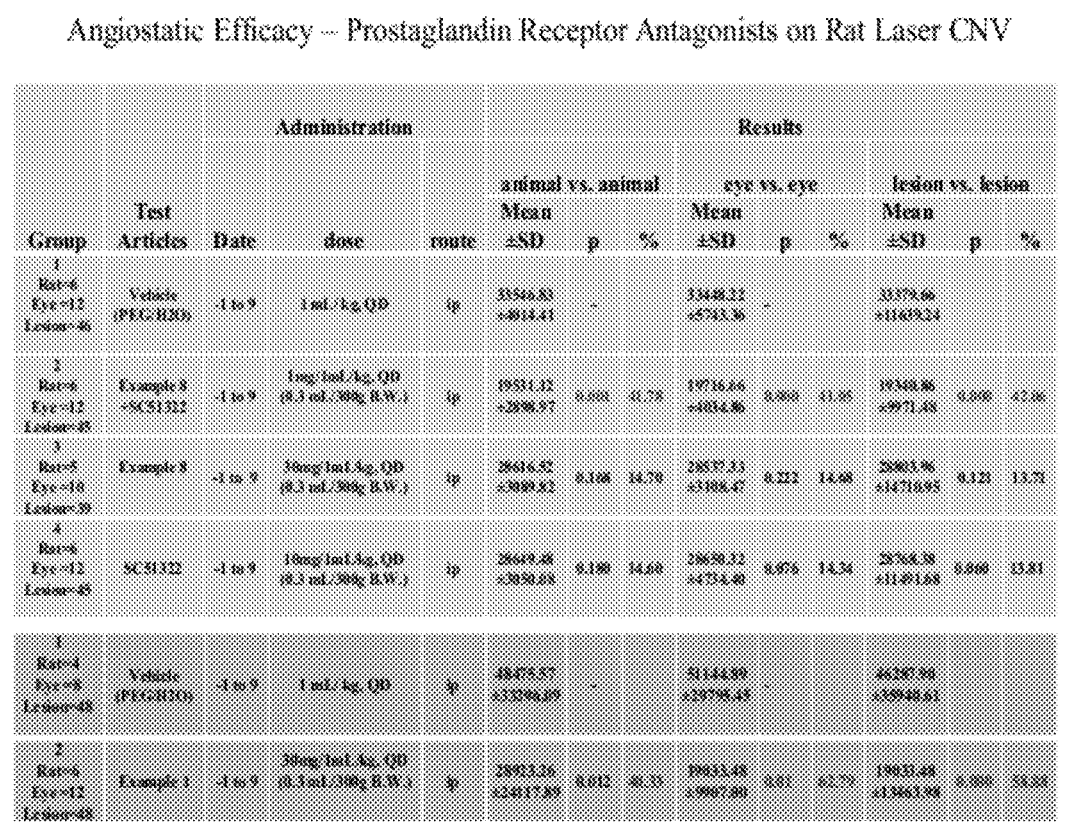

As shown in FIG. 15 (Angiostatic Efficacy—Prostaglandin Receptor Antagonists on Rat Laser CNV) the compound of EXAMPLE 1 obtains a better clinical score than any of the comparators except the combination of 3-(2-{(1S,2R,3S)-3-[4-(4-Cyclohexyl-butylcarbamoyl)-oxazol-2-yl]-7-oxa-bicyclo[2.2.1]hept-2-ylmethyl}-4-fluoro-phenyl)-propionic acid and SC-51322. In addition, since it has been found that the combination of 3-(2-{(1S,2R,3S)-3-[4-(4-Cyclohexyl-butylcarbamoyl)-oxazol-2-yl]-7-oxa-bicyclo[2.2.1]hept-2-ylmethyl}-4-fluoro-phenyl)-propionic acid and SC-51322 inhibits neovascularization, it is shown again that the compound of EXAMPLE 1, which has the same biological profile as the combination of 3-(2-{(1S,2R,3S)-3-[4-(4-Cyclohexyl-butylcarbamoyl)-oxazol-2-yl]-7-oxa-bicyclo[2.2.1]hept-2-ylmethyl}-4-fluoro-phenyl)-propionic acid and SC-51322, would also be effective for treating neovascularization. Furthermore, as representative of the other compounds utilized in the pharmaceutical compositions and methods of treatment of this invention, said other compounds will also be useful for treating and/or preventing neovascularization.

The present invention is not to be limited in scope by the exemplified embodiments, which are only intended as illustrations of specific aspects of the invention. Various modifications of the invention, in addition to those disclosed herein, will be apparent to those skilled in the art by a careful reading of the specification, including the claims, as originally filed. It is intended that all such modifications will fall within the scope of the appended claims.

What is claimed is:
1. A method for treating inflammation in a patient in need thereof comprising administering to said patient an effective amount of a compound selected from the group consisting of:

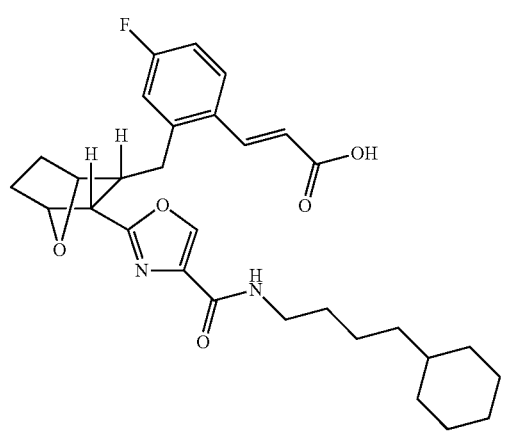

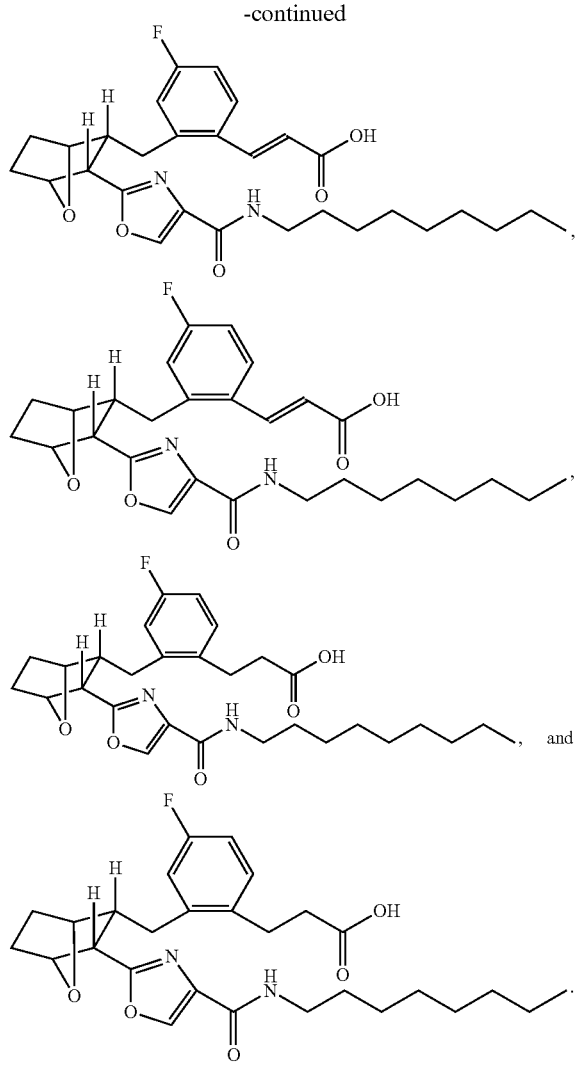

2. The method of claim 1, wherein said method comprises decreasing the secretion of ENA-78 in a patient.

3. The method of claim 1, wherein said method comprises decreasing the secretion of IL-8 in a patient.

4. The method of claim 1, wherein said method comprises decreasing the secretion of MCP-1 in a patient.

5. The method of claim 1, wherein said method comprises decreasing the secretion of PAI-1 in a patient.

6. The method of claim 1, wherein said method comprises decreasing the secretion of CD-40 in a patient.

7. The method of claim 1, wherein said method comprises decreasing the secretion of G-C-SF in a patient.

8. The method of claim 1, wherein said method comprises decreasing the secretion of GM-CSF in a patient.

9. The method of claim 1, wherein said method comprises decreasing the secretion of IL-1α in a patient.

10. The method of claim 1, wherein said method comprises decreasing the secretion of IL-18 in a patient.

11. The method of claim 1, wherein said method comprises decreasing the secretion of MDC in a patient.

12. The method of claim 1, wherein said method comprises decreasing the secretion of RANTES in a patient.

13. The method of claim 1, wherein said compound is at least as effective as COXIBs and NSAIDs in treating inflammation in a patient in need of such treatment, without causing cardiovascular, renal and/or gastro-intestinal side effects.

14. A method for decreasing the secretion of a cytokine selected from the group consisting of ENA-78, IL-8, MCP-1, PAI-1, TNFα, CD-40, G-CSF, GM-CSF, IL-1α, IL-18, MCD and RANTES in a patient in need thereof comprising administering to a patient an effective amount of a compound selected from the group consisting of:

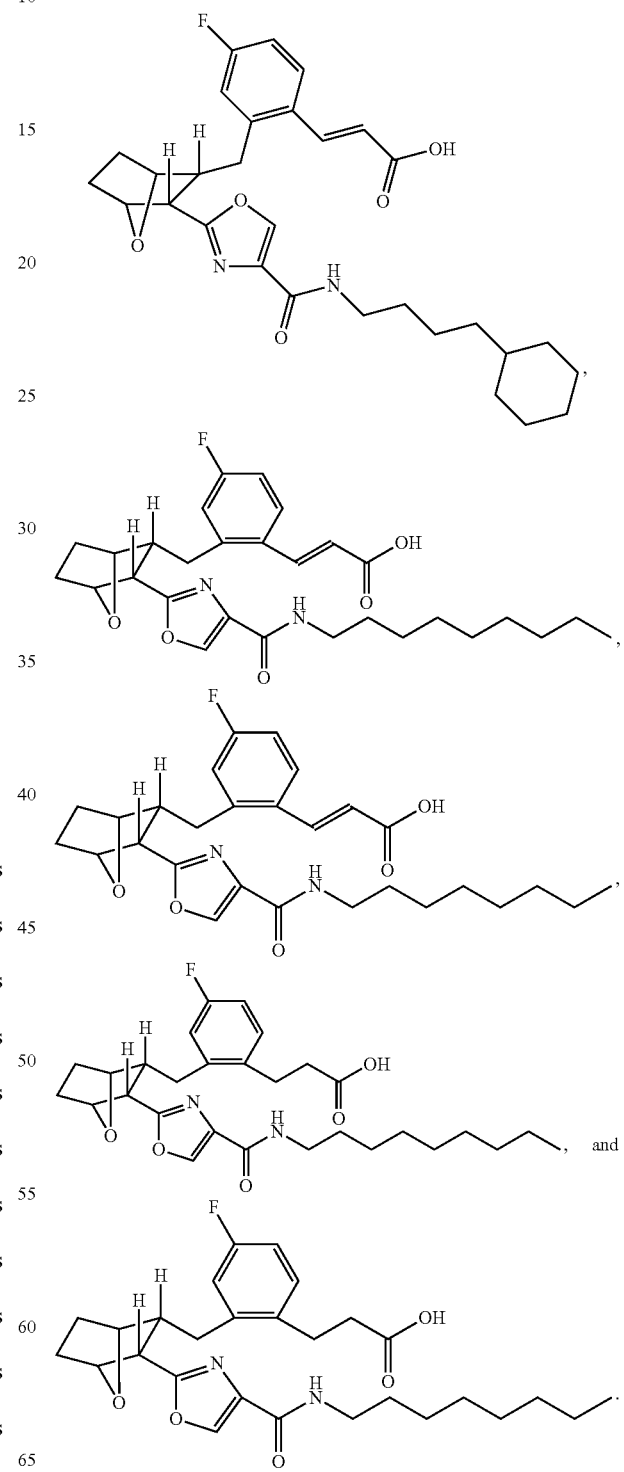

15. A method according to claim 14, wherein said cytokine is ENA-78 and said compound is administered for treating rheumatoid arthritis.

16. A method according to claim 14, wherein said cytokine is IL-8 and said compound is administered for treating rheumatoid arthritis.

17. A method according to claim 14, wherein said cytokine is MCP-1 and said compound is administered for treating inflammatory diseases selected from the group consisting of RA rheumatoid arthritus, psoriasis, and atherosclerosis; atopic dermatitis, renal disease; pleurisy; allergy and asthma; colitis; endometriosis; polymyositis and dermatomyositis; uveitis; restenosis; brain inflammation and obesity; diabetes and diabetes-induced atherosclerosis and MCP-1/CCR2-mediated multiple inflammatory diseases.

18. A method according to claim 14, wherein said cytokine is CD-40 and said compound is administered for treating rheumatoid arthritis, inflammation, vascular inflammation, post-traumatic inflammation, brain inflammation, allergic inflammation, lung inflammation, thrombosis and atherosclerosis, chronic renal failure, chronic liver diseases, Alzheimer's disease and systemic sclerosis.

\* \* \* \* \*